US012333720B2

(12) United States Patent
Haacke et al.

(10) Patent No.: US 12,333,720 B2
(45) Date of Patent: *Jun. 17, 2025

(54) SYSTEMS AND METHODS FOR TEMPLATE-BASED AUTOMATIC DETECTION OF ANATOMICAL STRUCTURES

(71) Applicant: SpinTech, Inc., Bingham Farms, MI (US)

(72) Inventors: Ewart Mark Haacke, Grosse Pointe Farms, MI (US); Ying Wang, Troy, MI (US)

(73) Assignee: Spin Tech, Inc., Bingham Farms, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/316,340

(22) Filed: May 12, 2023

(65) Prior Publication Data

US 2023/0281814 A1 Sep. 7, 2023

Related U.S. Application Data

(63) Continuation of application No. 17/735,287, filed on May 3, 2022, now Pat. No. 11,651,490, which is a (Continued)

(51) Int. Cl.
*G06T 7/00* (2017.01)
*A61B 5/00* (2006.01)
(Continued)

(52) U.S. Cl.
CPC .......... *G06T 7/0012* (2013.01); *A61B 5/055* (2013.01); *A61B 5/7253* (2013.01);
(Continued)

(58) Field of Classification Search
CPC . G06T 7/0012; G06T 3/18; G06T 7/11; G06T 7/62; G06T 2207/10088;
(Continued)

(56) References Cited

U.S. PATENT DOCUMENTS

| 6,757,442 B1 | 6/2004 | Avinash | |
|---|---|---|---|
| 11,651,490 B2* | 5/2023 | Haacke | ...................... G06T 7/12 382/131 |

(Continued)

FOREIGN PATENT DOCUMENTS

| EP | 0 610 916 A2 | 8/1994 |
|---|---|---|
| JP | 2004081424 A * | 3/2004 |

(Continued)

OTHER PUBLICATIONS

International Search Report and Written Opinion for PCT Appl. No. PCT/US2022/022576 mailed Jul. 29, 2022.

(Continued)

*Primary Examiner* — Jon Chang
(74) *Attorney, Agent, or Firm* — Foley & Lardner LLP

(57) ABSTRACT

Systems and methods for detecting anatomical structures include, for each training subject of a plurality of training subjects, a corresponding MR image, and generating an initial anatomical template based on a first training subject of the plurality of training subjects. A computing device can map MR images of the other training subjects onto a template space by applying a global transformation followed by a local transformation. The computing device can average the mapped MR images with the initial anatomical template to generate a final anatomical template and boundaries of an anatomical structure of interest can be drawn in the final anatomical template. The computing device can fine tune the boundaries using an edge detection algorithm. The final anatomical template can be used to identify boundaries of the anatomical structure(s) of interest automatically (e.g., without human intervention) in non-training subjects.

20 Claims, 20 Drawing Sheets

Related U.S. Application Data continuation of application No. PCT/US2022/022576, filed on Mar. 30, 2022.

(60) Provisional application No. 63/170,229, filed on Apr. 2, 2021.

(51) Int. Cl.
| | |
|---|---|
| A61B 5/055 | (2006.01) |
| G06T 3/18 | (2024.01) |
| G06T 7/11 | (2017.01) |
| G06T 7/12 | (2017.01) |
| G06T 7/149 | (2017.01) |
| G06T 7/62 | (2017.01) |
| G06V 10/25 | (2022.01) |
| G06V 10/774 | (2022.01) |

(52) U.S. Cl.
CPC ............... *A61B 5/7267* (2013.01); *G06T 3/18* (2024.01); *G06T 7/11* (2017.01); *G06T 7/62* (2017.01); *G06V 10/25* (2022.01); *G06V 10/774* (2022.01); *G06T 7/12* (2017.01); *G06T 7/149* (2017.01); *G06T 2207/10088* (2013.01); *G06T 2207/20081* (2013.01); *G06T 2207/20132* (2013.01); *G06T 2207/30004* (2013.01); *G06V 2201/03* (2022.01)

(58) Field of Classification Search
CPC . G06T 2207/20081; G06T 2207/20132; G06T 2207/30004; G06T 7/12; G06T 7/149; G06T 2207/30016; G06V 10/25; G06V 10/774; G06V 2201/03; G06V 10/751; A61B 5/055; A61B 5/7253; A61B 5/7267; A61B 5/4082; A61B 2576/026; A61B 5/0042

See application file for complete search history.

(56) References Cited

U.S. PATENT DOCUMENTS

| | | | |
|---|---|---|---|
| 2007/0116357 A1 | 5/2007 | Dewaele | |
| 2009/0136108 A1* | 5/2009 | Badiei | G06T 7/149 |
| | | | 382/131 |
| 2010/0130832 A1 | 5/2010 | Lang et al. | |
| 2013/0259341 A1 | 10/2013 | Mountney et al. | |
| 2014/0126800 A1 | 5/2014 | Lang et al. | |
| 2016/0217576 A1 | 7/2016 | Kabus et al. | |
| 2021/0313045 A1 | 10/2021 | Wu et al. | |

FOREIGN PATENT DOCUMENTS

| | | |
|---|---|---|
| JP | 2004-509686 A | 4/2004 |
| JP | 6738003 B1 | 8/2020 |
| WO | WO-2021/034770 A1 | 2/2021 |

OTHER PUBLICATIONS

Lilly et al., "Automatic Contour Definition on Left Ventriculograms by Image Evidence and a Multiple Template-Based Model" IEEE Transactions on Medical Imaging, vol. 8, No. 2, Jun. 1989, pp. 173-185.

Salehi et al., "Real Time Deep Pose Estimation With Geodesic Loss for Image-to-Template Rigid Registration" IEEE Transactions on Medical Imaging, 38(2)470:481, Feb. 2019.

Sharm et al., "ROI Segmentation using Local Binary Image" IEEE International Conference on Control System, Computing and Engineering, Nov. 29, 2013, pp. 136-141.

Sushmitha et al., "Automated Segmentation Technique for Detection of Myocardial Contours in Cardiac MRI" International Conference on Communication and Electronic Systems, Jul. 17, 2019, pp. 986-991.

Mandal et al., "Structural Brain Atlases: Design, Rationale, and Applications in Normal and Pathological Cohorts", Journal of Alzheimer's Disease, vol. 31, No. s3, Aug. 18, 2024, pp. S169-S188.

Ariz, Mikel et al: "Dynamic Atlas-Based Segmentation and Quantification of Neuromelanin-Rich Brainstem Structures in Parkinson Disease" IEEE Transactions On Medical Imaging, IEEE, USA, vol. 38, No. 3, Mar. 1, 2019 (Mar. 1, 2019), pp. 813-823, XP011712624, ISSN: 0278-0062, DOI: 10.1109/TMI.2018.2872852.

Daryanani, Aditya et al: "A comparison study of atlas-based 3D cardiac MRI segmentation: global versus global and local transformations", Progress in Biomedical Optics and Imaging, SPIE—International Society for Optical Engineering, Bellingham, WA, US, vol. 9786, Mar. 18, 2016 (Mar. 18, 2016), pp. 978624-978624, XP060069365, ISSN: 1605-7422, DOI: 10.1117/12.2217883 ISBN: 978-1-5106-0027-0.

European Search Report on EP 22782103 dated Jan. 29, 2025.

* cited by examiner

SYSTEMS AND METHODS FOR TEMPLATE-BASED AUTOMATIC DETECTION OF ANATOMICAL STRUCTURES

CROSS REFERENCE TO RELATED APPLICATIONS

This application is a continuation of U.S. application Ser. No. 17/735,287 filed on May 3, 2022, which issued as U.S. Pat. No. 11,651,490 on May 16, 2023, and is a continuation of International Application No. PCT/US2022/022576 filed Mar. 30, 2022, which claims priority to and the benefit of the U.S. provisional application No. 63/170,229 filed on Apr. 2, 2021, and titled "SYSTEMS AND METHODS FOR AUTOMATIC TEMPLATE-BASED DETECTION OF ANATOMICAL STRUCTURES," the contents of which are incorporated by reference herein in their entireties.

FIELD OF THE DISCLOSURE

The present disclosure relates generally to the field of detecting or identifying the boundaries of anatomical structures. Specifically, this disclosure relates to methods and systems for generating standardized templates and using such templates to automatically detect or identify the boundaries of anatomical structures.

BACKGROUND

One disease that calls for the identification of the boundaries of anatomical structures is the Parkinson's disease (PD), which is a chronic progressive neurodegenerative disorder affecting approximately 1% of individuals over 60 years of age PD is characterized pathologically by early neurodegeneration of neuromelanin (NM) in the substantia nigra pars compacta (SNpc) and increased iron deposition in the substantia nigra (SN). Degeneration of the SN is a hallmark of the progression of a number of neurodegenerative diseases. Extensive neuronal loss of SNpc also occurs in atypical parkinsonian disorders including progressive supranuclear palsy (PSP) and multiple system atrophy (MSA), although different subregions of the SN are affected in these disorders.

The SN is composed of two anatomically and functionally distinct regions, the SN pars reticulata (SNpr) and the SNpc. The SNpc contains a dense distribution of NM containing dopaminergic neurons while iron content tends to be higher in the SNpr. However, clusters of SNpc dopaminergic neurons (known as nigrosomes) are deeply embedded within the SNpr, thus the boundary between the SNpr and the SNpc is difficult to delineate especially in the caudal region of the SN. The regional selectivity of PD is relatively specific with a 50% to 70% loss of pigmented neurons in the ventral lateral tier of the SNpc (at the onset of symptoms). For the SN, iron deposition and volume changes of the red nucleus (RN) and subthalamic nucleus (STN) are reported to be associated with the disease status and rate of progression, and also serve as important targets for deep brain stimulation (DBS) treatment in PD patients.

SUMMARY OF THE DISCLOSURE

According to at least one aspect, a magnetic resonance imaging (MRI) system comprises a MRI scanner configured to acquire magnetic resonance (MR) data, at least one processor and a memory with computer code instructions stored thereon. The computer code instructions, when executed by the at least one processor, cause the at least one processor to acquire, via the MRI scanner, for each training subject of a plurality of training subjects, a corresponding MR image with contrast illustrating one or more anatomical structures of interest. The at least one processor can generate an initial anatomical template image based on a first MR data of a first training subject of the plurality of training subjects. The initial anatomical template image can define a template space. For each training subject of the plurality of training subjects other than the first training subject, the at least one processor can (i) apply a global transformation to the MR image of the training subject to generate a first morphed version of the MR image representing a first estimate of MR data of the training subject in the template space, and (ii) apply a local transformation to the first morphed version of the MR image of the training subject to generate a second morphed version of the MR image representing a second estimate of the MR data of the training subject in the template space. The at least one processor can average the initial anatomical template image and the second morphed versions of the MR images of the plurality of training subjects to generate a final anatomical template image. The at least one processor can delineate the boundaries of the one or more anatomical structures of interest in the final anatomical template and use the final anatomical template to identify the boundaries of the one or more anatomical structures of interest for other non-training subjects.

According to at least one aspect, a method can include acquiring, via the MRI scanner, for each training subject of a plurality of training subjects, a corresponding MR image with contrast illustrating one or more anatomical structures of interest. The method can include a computing device generating an initial anatomical template image based on a first MR data of a first training subject of the plurality of training subjects. The initial anatomical template image can define a template space. For each training subject of the plurality of training subjects other than the first training subject, the computing device can (i) apply a global transformation to the MR image of the training subject to generate a first morphed version of the MR image representing a first estimate of MR data of the training subject in the template space, and (ii) apply a local transformation to the first morphed version of the MR image of the training subject to generate a second morphed version of the MR image representing a second estimate of the MR data of the training subject in the template space. The method can include averaging the initial anatomical template image and the second morphed versions of the MR images of the plurality of training subjects other than the first training subject, to generate a final anatomical template image. The method can include delineating the boundaries of the one or more anatomical structures of interest in the final anatomical template, and using the final anatomical template to identify the boundaries of the one or more anatomical structures of interest for other non-training subjects.

According to at least one aspect, a non-transitory computer-readable medium can include computer code instructions stored thereon. The computer code instructions, when executed by a processor, can cause the processor to acquire, via the MRI scanner, for each training subject of a plurality of training subjects, a corresponding MR image with contrast illustrating one or more anatomical structures of interest. The processor can generate an initial anatomical template image based on a first MR data of a first training subject of the plurality of training subjects. The initial anatomical template image can define a template space. For each training subject of the plurality of training subjects other than the first training subject, the processor can (i) apply a global transformation to the MR image of the training subject to generate a first morphed version of the MR image representing a first estimate of MR data of the training subject in the template space, and (ii) apply a local transformation to the first morphed version of the MR image of the training subject to generate a second morphed version of the MR image representing a second estimate of the MR data of the training subject in the template space. The processor can average the initial anatomical template image and the second morphed versions of the MR images of the plurality of training subjects other than the first training subject, to generate a final anatomical template image. The processor can delineate the boundaries of the one or more anatomical structures of interest in the final anatomical template, and use the final anatomical template to identify the boundaries of the one or more anatomical structures of interest for other non-training subjects.

DETAILED DESCRIPTION

Figure 1:
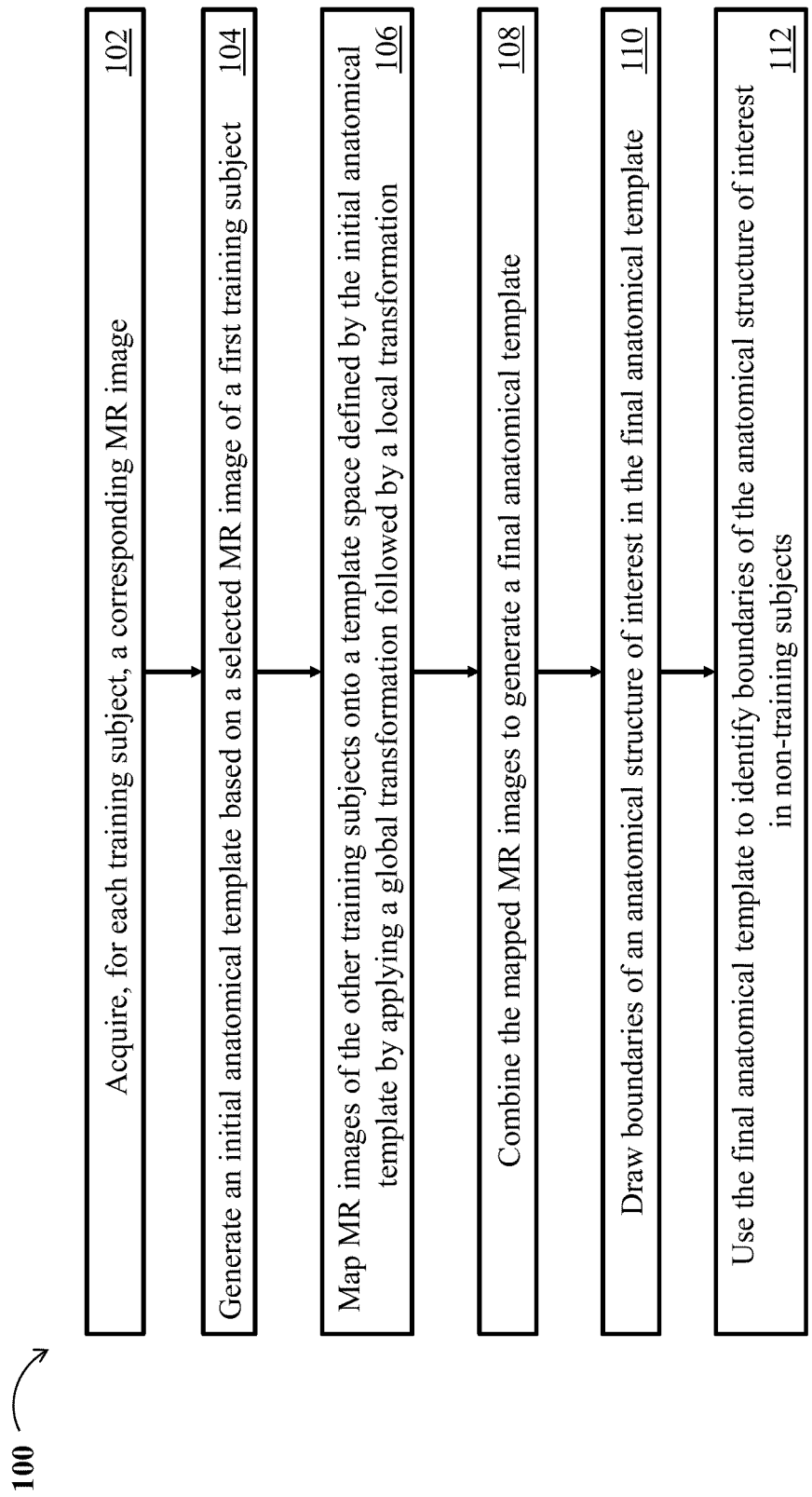
FIG. 1 is a flowchart illustrating a method for generating an anatomical template, according to inventive concepts of this disclosure.

For some diseases, such as Parkinson's disease (PD), information about the state of the disease and/or information useful in some treatment can be deduced from the volume or other geometrical characteristics of some anatomical structures. In the case of PD, for the substantia nigra (SN), iron deposition and volume changes of the red nucleus (RN) and subthalamic nucleus (STN) are known to be associated with the disease status and rate of progression, and also serve as important targets for deep brain stimulation (DBS) treatment in PD patients. Therefore, an accurate and comprehensive in-vivo delineation of the SN and its subregions, the RN and the STN could be useful to fully investigate the composition of iron and neuromelanin (NM) changes in PD and other movement disorders affecting the midbrain Therefore, an accurate in-vivo delineation of the SN, its subregions and other midbrain structures such as the red nucleus (RN) and subthalamic nucleus (STN) could be useful to fully investigate iron and NM changes in PD.

To date, many studies still use manual or semi-automated approaches to demarcate the deep brain grey matter. However, manual segmentation is time-consuming, especially when large amounts of data need to be evaluated. And, unless the raters are well trained, manual drawings are less reliably duplicated from individual to individual or site to site. Some approaches for in-vivo delineation can include the use of templates to map iron and NM content. In such approaches, creating standardized templates may have a significant impact on (a) recognizing changes in the distribution of iron and NM, (b) automatically calculating volumes associated with such distributions, (c) quantifying the iron content and changes in NM signal and (d) the reliability of these measurements. Anatomical templates of the SN using conventional structural MR sequences have been used previously in some studies. T1 weighted (T1W) and T2 weighted (T2W) images can be employed to create a high-resolution probabilistic in vivo subcortical nuclei atlas and have been able to segment the SN into the substantia nigra pars compacta (SNpc) and substantia nigra pars reticulata (SNpr). Such atlases, when based on images from a young adult population (e.g., mean±standard deviation age: 28.9±3.6 years), may not be suitable for studies on elderly subjects. Furthermore, both T1W and T2W contrast images cannot be easily used to delineate the highly inter-digitated boundaries between the SNpc and SNpr in elderly subjects. Based on the anatomical connection of the SN subregions to different parts of the brain, diffusion-based tractography can be used to segment the SN into the SNpc and SNpr or subdivide the SN/ventral tegmental area (VTA) into dorsomedial and ventrolateral subregions. However, the estimated structural connectivity has well-known biases and is highly dependent upon the data acquisition and fiber tracking algorithm and diffusion imaging suffers from low resolution data acquisition. Thus, direct visualization and segmentation of the SN and its subregions using high resolution imaging would be a more accurate option especially when it comes to detecting subtle pathological changes of the SN.

One approach to determine the boundaries of the midbrain nuclei and study pathological changes in PD patients may be based on the use of T2* weighted gradient echo (GRE) imaging and susceptibility weighted imaging (SWI) where iron containing regions appear hypointense. On the other hand, the development of quantitative susceptibility mapping (QSM) enables the quantification of iron stored in ferritin and hemosiderin. QSM-based techniques indicate that the tissue magnetic susceptibility correlates well with brain iron in P) patients. In addition, QSM is superior to traditional T2*W imaging in preoperative target guidance of DBS. However, QSM alone is not able to separate the SNpc from the SNpr because both the SNpc and SNpr contain iron. This limitation can be solved by using neuromelanin-sensitive MRI (NM-MRI) developed in the last few years. The SNpc and ventral tegmental area (VTA) are mainly composed of the dopaminergic neurons containing NM, but the SNpr is not. Hence, the hyperintense signal seen in NM-MRI in the midbrain is spatially associated with the SNpc and VTA region (and this has been validated by postmortem histological studies). Thus, the overlap between the NM volume (SNpc plus VTA) and iron containing SN volume (SNpc plus SNpr) is thought to represent the SNpc.

So far, existing approaches do not accurately and reliably segment the SNpc using QSM and/or NM-MRI imaging. The SN atlas may be obtained using only QSM Alternatively, a NM template based on the NM-MRI imaging, e.g., created using manual drawing, automated segmentation or artificial intelligence, may be employed. The goal of using a template would be to make the identification of the boundaries easier. However, template mapping is not perfect and the ideal space to mark the boundaries is in the original pristine data space. Whether in template space (a standard fixed brain or volunteer to which all other brains are mapped) or the original space (the original brain imaging data for a given individual), simple thresholding methods have their drawbacks. Setting the threshold to relatively high or relatively low values can lead to dramatic changes in the estimated volume of the NM or iron content, especially in PD patients with severe NM degeneration and iron deposition in the SN. Variable contrast in the images can also make it difficult to use a number of algorithms such as region growing. Despite the fact that the SN has high iron content compared to the surrounding regions, it is not uniformly distributed and there are reductions in iron in the nigrosome 1 (N1) territory. Gaps in the structure such as the N1 territory can also add to the difficulty of automatically segmenting the SN and NM regions of interest (ROIs).

In the current disclosure, systems and methods for detecting anatomical structures can include creating both NM and iron templates using high resolution imaging from a single multi-echo NM MRI sequence and calculating the boundaries of each structure in template space. Specifically, both NM and iron templates from a single, high resolution, NM MRI sequence can be used to (i) calculate the boundaries of each structure in template space, (ii) map these boundaries back to the original space and then (iii) fine tune the boundaries in the original space using a dynamic programming algorithm (DPA) to match the details of each individual's NM and SN features. Experimental results for the NM of the SN and the iron content for the SN, STN and RN all indicate a strong agreement in terms of DICE values and volume ratios with the former being 0.85, 0.87, 0.75 and 0.92 and the latter being 0.99, 0.95, 0.89, 1.05, respectively. These high quality results indicate that it is possible to confidently measure tissue properties such as volumes, iron content and neuromelanin content. Multiple sequences sensitive to NM and iron can also be used but then co-registration between the two may be needed.

Referring to FIG. 1, a flowchart illustrating a method 100 for generating an anatomical template is shown, according to inventive concepts of this disclosure. The method 100 can include a computing device or system acquiring, for each training subject of a plurality of training subjects, a corresponding MR image (STEP 102), and generating an initial anatomical template based on a selected MR image of a first training subject of the plurality of training subjects (STEP 104) The method 100 can include the computing device or system mapping MR images of the other training subjects onto a template space defined by the initial anatomical template by applying a global transformation followed by a local transformation (STEP 106). The method 100 can include averaging the mapped MR images and the initial anatomical template to generate a final anatomical template (STEP 108). The method 100 can include drawing boundaries of an anatomical structure of interest in the final anatomical template (STEP 110). The method 100 can include using the final anatomical template to identify boundaries of the anatomical structure(s) of interest in non-training subjects (STEP 112).

The method 100 can include the computing device or system acquiring, for each training subject of a plurality of training subjects, a corresponding MR image (STEP 102). The training subjects can be selected based on some predefined criteria, such as age, health state or conditions and/or history of each subject. The study described herein was approved by the local ethics committee and all subjects signed a consent form. Eighty seven healthy subjects (mean age: 63.4±6.2 years old, range: 45-81 years, 53 females) were recruited from the local community by advertisement. Exclusion criteria for potential training subjects included (a) structural abnormalities, such as tumor, subdural hematoma, or contusion from a previous head trauma, (b) a history of stroke, addiction, neurologic or psychiatric disease, and (c) large-vessel disease and/or diseases with large volume white matter lesions (e.g., Fazekas grade III).

The MR images of the training subjects can be acquired via an MRI scanner. For example, in the conducted study, MR imaging was carried out on a 3T Ingenia scanner (Philips Healthcare, Netherlands) using a 15-channel head array coil. The imaging parameters of the 3D gradient echo SWI sequence with an activated magnetization transfer contrast (MIC) pulse include time to echo (TE)=7.5 ms, $\Delta TE$=7.5 ms with a total of 7 echoes, repetition time (TR)=62 ms, flip angle:=30°, pixel bandwidth=174 Hz/pixel, matrix size=384×144, slice thickness=2 mm, slice number=64, spatial in-plane resolution=0.67×1.34 mm$^2$ interpolated to 0.67×0.67 mm$^2$, a sense factor of 2, elliptical sampling of k-space and a total scan time equal to 4 minutes and 47 seconds. The magnetization transfer (MT) on-resonance radio-frequency pulse used a nominal flip angle of 90°, zero frequency offset, and a set of 3-block pulses each of duration 1.914 milliseconds (ms). The minimum allowed TR was used based on specific absorption rate safety considerations. Due to this long repeat time of 62 ms, 7 echoes were collected.

In some implementations, the computing device or system can use the first echo of the MTC-SWI magnitude image (TE=7.5 ms) to delineate the NM content since that echo provides the key MT contrast. The computing device or system can use the second echo (TE=15 ms), or a combination of QSM images from 2 or more echoes, for QSM reconstruction to evaluate iron deposition in the SN. The computing device or system can create susceptibility maps by (i) using a brain extraction tool, BET, to segment the brain, (ii) using a 31) phase unwrapping algorithm (3DSRNCP) to unwrap the original phase data, (iii) using sophisticated harmonic artifact reduction (SHARP) to remove unwanted background fields, and (iv) using a truncated k-space division (TKD) based inverse filtering technique with an iterative approach to reconstruct the final QSM maps.

Manual region of interest (ROI) segmentation can be employed in tracing boundaries of anatomical structures of interest. To measure the NM and iron content, the regions of interest (ROIs) for the NM, SN, RN and STN can be manually traced by a single rater on MTC magnitude and QSM maps zoomed by a factor of four using SPIN software (SpinTech, Inc., Bingham Farms, MI, USA). The NM-based SN boundaries can be traced starting from the last caudal slice for 4 to 5 slices cranially until the NM is no longer visible when 2 mm thick slices are used (or over a total thickness of 8 to 10 mm). The iron-based SN boundaries can be traced starting from one slice below the most cranial slice where the subthalamic nucleus is visible and can continue for 4-6 consecutive slices to the most caudal slice, or over a total thickness of 8 to 12 mm. The RN ROIs can be outlined starting from the last caudal slice and continuing for 3 to 4 slices cranially, or over a total thickness of 6 to 8 mm. The STN ROIs can be traced for 2 slices cranially, or over a total thickness of about 4 mm. For all the ROIs, a dynamic programming algorithm (DPA) can be used to determine the final boundaries to alleviate the subjective bias. All these boundaries can then be reviewed one by one by a second rater and modified accordingly in consensus with the first reviewer.

One should appreciate that the data acquisition parameters and/or the data processing scenarios described above represent an example implementation provided for illustrative, but not limiting purposes. For instance, the slice numbers provided above are specific to a given resolution with a slice thickness equal to 2 mm. If one were to use a 1 mm thick slice all these slice numbers would double. Furthermore, while the description focuses mainly on the application to PD and anatomical structures of the midbrain, the methods and techniques described herein can also be applied in other applications or to other anatomical regions, such as the deep cerebellar nuclei or the striatum and caudate nucleus or any other areas of interest.

In some implementations the computing device or system can cause the MR scanner to perform MR data acquisition, e.g., 7.5 ms echo time MTC data acquisition starting with the original full brain 64 slice data, for each training subject of the plurality of training subjects. The MR scanner can construct, for each training subject, a corresponding three-dimension (3-D) image (or a plurality of corresponding two-dimension (2-D) images) based on the corresponding acquired MR data. In acquiring the MR data for the plurality of training subjects, the MR scanner can be configured with parameters selected to generate MR images with/having contrast illustrating one or more anatomical structures of interest (e.g., SN, RN and/or STN regions). The MR scanner can acquire NM-MRI data (e g, NM-MRI image(s)) and/or QSM data (QSM image(s)) for each training subject of the plurality of training subjects.

The method 100 can include the computing device or system generating an initial anatomical template based on a selected MR image of a first training subject of the plurality of training subjects (STEP 104). The computing device or system (or a user thereof) can select a first 3-D MR image (or corresponding 2-D images) of a first training subject among the MR images of the plurality of training subjects. The selection can be random or according to predefined preferences or criteria. In generating the initial anatomical template, the computing device or system can zoom the first 3-D image (or corresponding 2-D images) in-plane, e.g., by a factor of two, four or higher factor depending on the desired final resolution, for all acquired slices of the first training subject. This step can also include interpolating in the slice select direction to obtain isotropic resolution in the template space. The template space can be defined in the desired resolution or a resolution higher than that of the acquired MR data. In some implementations, the computing device or system can generate an initial NM-MRI template and an initial QSM template based on NM data and QSM data of the first training subject, respectively. As discussed in further detail below, the computing device or system can use the initial anatomical template to map MR images of the other training subjects to the template space.

The method 100 can include the computing device or system mapping MR images of the other training subjects onto a template space defined by the initial anatomical template by applying a global transformation followed by a local transformation (STEP 106). The computing device or system can apply the global transformation and the local transformation to each of the images of the other training subjects (other than the first training subject). The computing device or system can apply the global transformation, after zooming each MR image of the MR images in-plane by a zooming factor (e.g., two, four or higher factor) for all slices, over a series of slices covering the region of interest within each MR image of the other training subjects, other than the first training subject. For example, for the midbrain, the series of slices covering the region of interest can be a set of 50 central slices when the slice thickness is 2 mm. The global transformation can include a rigid transformation followed by an affine transformation with b-spline interpolation applied, for example, using the insight segmentation and registration toolkit freeware (ITK). The computing device or system can apply the same global transformation to map the QSM data for each of the other training subjects to the initial QSM template.

The computing device or system can apply the global transformation to each MR image (e.g., QSM image and/or NM-MRI image) of the other training subjects to generate a corresponding first morphed version of the MR image representing a corresponding first estimate of the initial template in the template space. That is, the global transformation is used to match each MR image of the other training subjects (other than the first training subject) to the initial anatomical template in the template space. However, the global transformation usually does not provide an accurate match with the anatomical structures in the initial anatomical template.

To improve the matching between transformed MR images and the initial anatomical template in the template space, the computing device or system can apply the local transformation to the first morphed versions of the MR images of the other training subjects (other than the first training subject). The computing device or system can crop the first morphed versions of the MR images both in-plane to cover the midbrain and to about 16 slices (e.g., when slice thickness is 2 mm) to ensure coverage of the midbrain territory. The computing device or system can apply the local transformation to the cropped image volumes to generate second morphed versions of the MR images of the other training subjects. For each MR image of training subject (other than the training subject), the corresponding second morphed version represents a better matching with the initial anatomical template in the template space.

As an example implementation, a total of 26 training subjects can be used. The computing device or system can select the MR data of one of these training subjects (referred to herein as the first training subject) to generate the initial anatomical template. The computing device or system can then apply the global and local transformations to the MR data of each of the other 25 training subjects to map MR data of each of the other 25 training subjects, after applying the global and local transformations, to the initial anatomical template in the template space.

The method 100 can include averaging the mapped MR images and the initial anatomical template to generate a final anatomical template (STEP 108). The computing device or system can average the mapped MR images with the initial anatomical template to generate the final anatomical template. The result is an averaged template defined, for example, for the 16 slices encompassing the midbrain territory. The averaged anatomical template has more representative boundaries of anatomical structures of interest compared to the initial anatomical template generated based on MR data of a single training subject or compared to a template generated by averaging the first morphed versions and the initial anatomical template. The computing device or system can linearly interpolate the averaged anatomical template in the slice select direction, for example, to create a template with 0.167 isotropic resolution (for a total of 192 slices).

The method 100 can include drawing boundaries of an anatomical structure of interest on the final anatomical template (STEP 110). The tracing of the boundaries of the anatomical structures (or regions) of interest can be performed manually, for example, by a physician or a radiologist. The final anatomical template generated according to STEPs 102-108 of method 100 depicts enhanced contrast of the anatomical structures of interest, therefore, allowing for more precise tracing of the boundaries of such structures.

In the final anatomical template(s), the average values can be viewed as indicative of the probability map for finding the boundaries. In some implementations, more than one final anatomical template can be generated. For example, one QSM template and one NM-MRI template can be generated based on NM data and QSM data, respectively. In some implementations, the boundaries for the NM, red nucleus (RN), SN and subthalamic nucleus (STN) can be all drawn manually. For the neuromelanin (NM) data, slices 44-98 from the 192 total interpolated slices can be used to draw the boundaries, while for the QSM data slices 44-126 can be used. The actual choice of slice numbers depends on the resolution used and the degree of interpolation.

The method 100 can further include using a boundary detection algorithm to fine tune the boundaries of the anatomical structures of interest in the final anatomical template. The boundary detection algorithm can be implemented as a dynamic programming algorithm (DPA). The computing device or system can run (or execute) the DPA for boundary detection to finalize the template boundaries. The DPA can use a cost function dependent on the local radius of curvature and signal gradients. Further details of this algorithm are provided below.

The method 100 can include the computing device or system using the final anatomical template to identify boundaries of the anatomical structure(s) of interest in non-training subjects (STEP 112). The use of the final anatomical template to identify boundaries of the anatomical structure(s) of interest in non-training subjects is discussed in detail with regard to FIG. 2 below.

Figure 2:
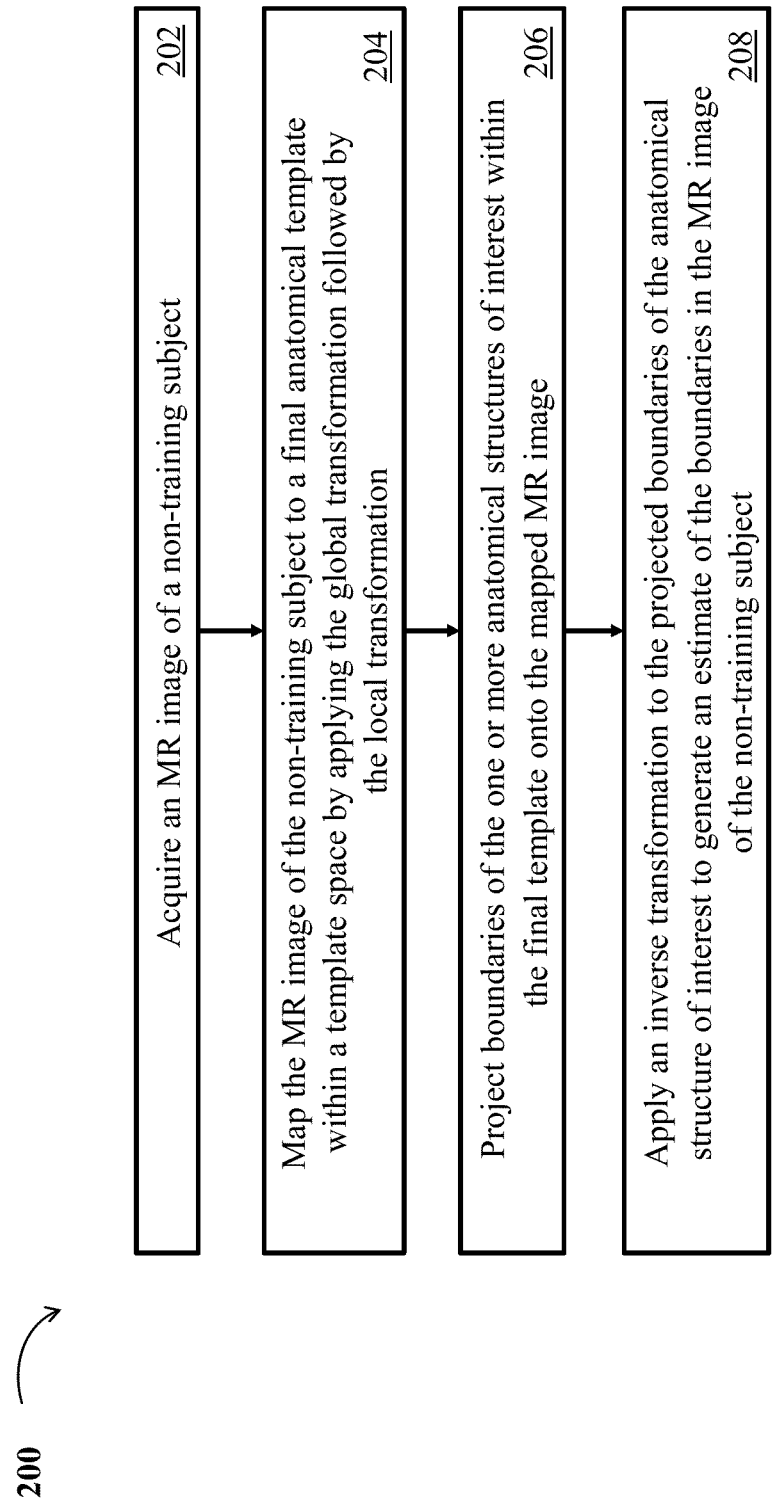
FIG. 2 is a flowchart illustrating a method of automatic template-based identification of characteristics of anatomical structures, according to inventive concepts of this disclosure.

Referring now to FIG. 2, a flowchart illustrating a method 200 of automatic template-based identification of characteristics of anatomical structures is shown, according to inventive concepts of this disclosure. The method 200 can include acquiring an MR image (or MR data) of a non-training subject (STEP 202). The method 200 can include mapping the MR image of the non-training subject to a final anatomical template within a template space by applying a global transformation followed by a local transformation (STEP 204). The method 200 can include projecting boundaries of one or more anatomical structures of interest from the final anatomical template onto the mapped MR image of the non-training subject (STEP 206). The method 200 can also include applying an inverse transformation to the projected boundaries of the anatomical structure(s) of interest to generate an estimate of the boundaries in the MR image of the non-training subject (STEP 208).

The method 200 allows for automatic identification of boundaries of the anatomical structure(s) of interest for non-training subjects, using the final anatomical template. While the method 100 for generating the anatomical template may involve human intervention (e.g., manually drawing the boundaries at STEP 110), the method 200 for automatic identification of boundaries of the anatomical structure(s) of interest for non-training subjects can be performed/executed automatically without any human intervention.

The method 200 can include the computing device acquiring an MR image (or MR data) of a non-training subject (STEP 202). The MR scanner can acquire MR data (e.g., a 3-D MR image or a plurality of 2-D MR images) of the non-training subject in a similar way as discussed above with regard to STEP 102 of method 100 of FIG. 1. The non-raining subject can be a person (e.g., a patient or research subject) who does not belong to the plurality of training subjects used in method 100 to generate the final anatomical template. The MR scanner can acquire NM data and/or QSM data of the non-training subject.

The method 200 can include mapping the MR image of the non-training subject to the final anatomical template within the template space by applying a global transformation followed by a local transformation (STEP 204) The global and the local transformations can be similar to those described with regard to STEP 106 of method 100 of FIG. 1. The computing device or system can first apply the global transformation to the MR image(s) (e.g., NM and QSM images) of the non-training subject to generate first morphed version(s) of the MR image(s) of the non-training subject.

After applying the global transformation, the computing device or system can crop the first morphed version(s) of the MR image(s) of the non-training subject. For instance, the computing device or system can label the RN in the two central slices of the template data and transform them back to the original full brain. If the RN is still only evident in two slices, the lowest slice is set to slice 10. If it is in 3 slices then the middle slice is set to slice 10. This provides for a means to best center the data prior to the final transformation back to the template space. The computing device or system can zoom the cropped image volume by a factor of 4 (or other zooming factor) in-plane and then apply the local transformation to the zoomed cropped image volume to obtain a second morphed version(s) of the MR image(s) of the non-training subject with an isotropic image (the transformation allowing for interpolation in the slice select direction as well as to make the image isotropic). The second morphed version(s) of the MR image(s) of the non-training subject represents a relatively good match of the final anatomical template in the template space. The interpolated in-plane resolution provides a more accurate means to estimate the final object size using the DPA algorithm.

The method 200 can include projecting boundaries of one or more anatomical structures of interest from the final anatomical template onto the mapped MR image of the non-training subject (STEP 206). Once the MR image(s) of the non-training subject is matched or mapped to the final anatomical template (by applying the global and local transformations), the computing device or system can project the boundaries of the anatomical structure(s) of interest drawn in the final anatomical template onto the second morphed version(s) of the MR image(s) of the non-training subject.

The method 200 can include applying an inverse transformation to the projected boundaries of the anatomical structure(s) of interest to generate an estimate of the boundaries in the MR image of the non-training subject (STEP 208). The inverse transform is performed to map the template boundaries of the anatomical structure(s) of interest back onto the midbrain (e.g., onto the original image space) of the non-training subject's MR image(s) However, there is no guarantee that the projected boundaries would fit well since everyone is different and template mapping is not perfect.

The method 200 can further include the computing device or system using the boundary detection algorithm (or DPA) to fine tune the boundaries of the anatomical structures of interest in the original acquired MR image(s) of the non-training subject. The computing device or system can apply thresholding to the region(s) inside the transformed boundaries for the QSM data to remove negative values, and can determine the corresponding centerline using image thinning. In order to best choose an initial starting point for the DPA, both an Otsu histogram analysis and a threshold based approach can be used to determine if the original boundary extended too far outside the structure(s) of interest. For the NM data, the computing device or system can determine the background intensity and a constant equal to four times the background standard deviation averaged over all the 25 training subjects (or training subjects other than the first training subject) that is added to create a threshold below which the signal was set to zero. For the QSM data, the starting threshold can be set to zero. When the Otsu threshold gives a value that caused pixels inside the structure(s) (or region(s)) of interest to be removed, the template transformed boundary can be shrunk accordingly. For the QSM data, if the Otsu threshold is greater than 30 ppb, the threshold can be set to 30 ppb. Finally, the computing device or system can modify the resulting boundaries once again using the same DPA used in the template space (as discussed above with regard to FIG. 1). This DPA, along with the RN boundaries, prevents leakage of the SN into the RN and with the help of the template boundaries can differentiate the STN from the SN.

Figure 3:
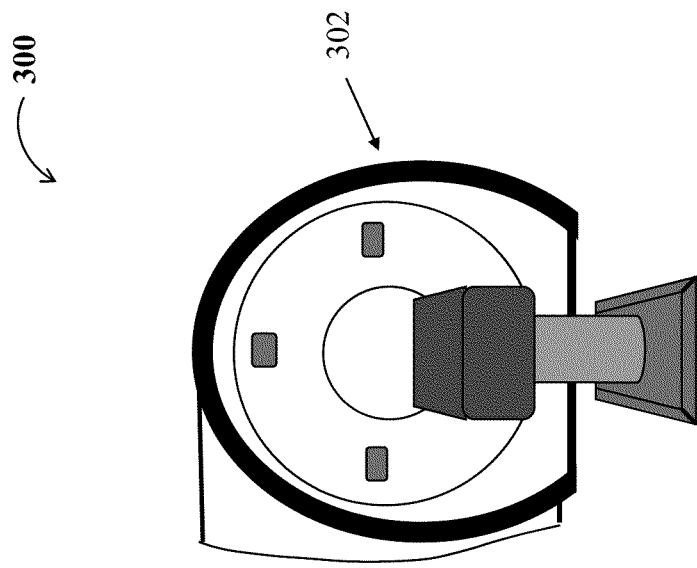
FIG. 3 shows a diagram illustrating a system for detecting or identifying the boundaries of anatomical structures, according to inventive concepts of this disclosure.
Figure 3:
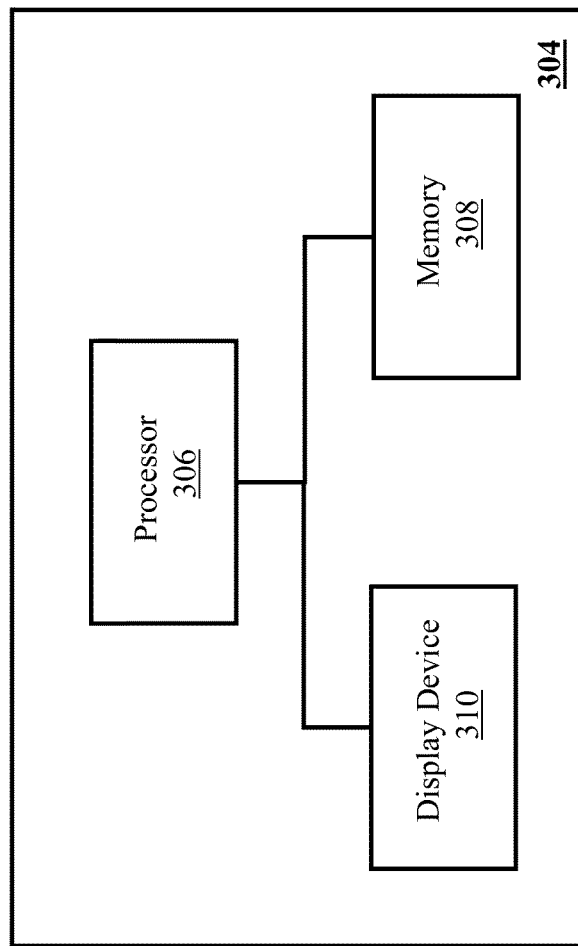

Referring to FIG. 3, a diagram illustrating a system 300 for detecting or identifying the boundaries of anatomical structures, according to inventive concepts of this disclosure. The system 300 can include a MR scanner 302 for acquiring MR data and a computing device 304 for processing the acquired MR data to detect or identify the boundaries of the anatomical structures. The computing device 304 can include a processor 306 and a memory 308. The memory 308 can store computer code instructions for execution by the processor 306. The computer code instructions, when executed by the processor 306, can cause the computing device 304 to perform method 100 and/or method 200 discussed above. The computing device 304 may further include a display device 310 to display MR images, output results of method 100 and/or method 200, or other data.

In some implementations, the computing device 304 can be an electronic device separate from the MR scanner 302. In such implementations, the computing device 304 may, or may not, be communicatively coupled to the MR scanner 302. For instance, the MR data acquired by the MR scanner 302 may be transferred to the computing device 304 via a flash memory, a compact disc (CD) or other storing device. If the computing device 304 is communicatively coupled to the MR scanner 302, the MR data acquired by the MR scanner 302 can be transferred to the computing device 304 via any communication link(s) between the MR scanner 302 and the computing device 304.

In some implementations, the computing device 304 can be integrated within the MR scanner 302. For instance, the processor 306, the memory 308 and/or the display device 310 can be integrated within the MR scanner 302. In such implementations, the MR scanner 302 can acquire the MR data and perform method 100 and/or method 200.

In summary, boundaries can be initially drawn manually in the template space for each of the SN, RN and STN and the system 300 or the computing device 304 can run DPA to fine tune the boundaries. The system 300 or the computing device 304 can map these boundaries back to the original space, and run DPA once again to provide the final boundaries, making this a fully automated process. After the manual drawings are made, the system 300 or the computing device 304 can run the DPA making the final boundary determination fully automatic. Using the final boundaries, the system 300 or the computing device 304 can calculate the volumes, signal intensities, susceptibility and/or overlap fraction.

The system 300 or the computing device 304 can calculate the overlap between the NM complex volume (SNpc plus VTA) and iron containing SN volume (SNpc and SNpr) by superimposing the two ROIs from the MTC and QSM data, respectively. The system 300 or the computing device 304 can normalize the overlap by the iron containing SN volume creating an overall overlap fraction (OOF) measure, which basically measures the SNpc fraction with respect to the entire SN volume, as shown below:

$$OOF = \frac{\sum_{slices\ where\ SN_{pc}\ is\ present} \text{volume of the intersection between } NM \text{ and } SN}{\sum_{slices\ where\ SN_{pc}\ is\ present} \text{volume of the iron containing } SN}$$

The process of generating the final anatomical template, described with regard to FIG. 1 above, was evaluated using MR data of various control subjects. The evaluation was based on comparison of the performance of the process of generating the final anatomical template to manually drawn boundaries of the anatomical structure(s) of interest.

A total of 87 healthy controls (HCs) were scanned. The SN, STN and RN were manually traced for all 87 cases. Of these, 30 (testing dataset: age range 66±7.2 years old, including 17 males and 13 females) were used for the initial training of the template approach described above Once all aspects of the algorithm were in place, we then validated the method with the next 57 cases (validation dataset: age range 61.9±5.0 years old, including 17 males and 40 females). In order to evaluate the performance of the anatomical template generation process, two measures were used. These are the DICE similarity coefficient, which shows the spatial overlap between the structures associated with the manual and template segmentation methods, and the volume ratio (VR) of the structure from the template volume divided by that of the manual segmentation.

Finally, all data were combined to produce the quantitative information regarding structural volumes, NM and iron content, and overlap between the SN and NM regions. The total iron content was calculated by summing the product of the volume and the mean susceptibility of the structure over all the slices that the structure was drawn on. Similarly, the total NM content was resulted from the sum of the product of NM volume and NM contrast over the corresponding slices.

Figure 4:
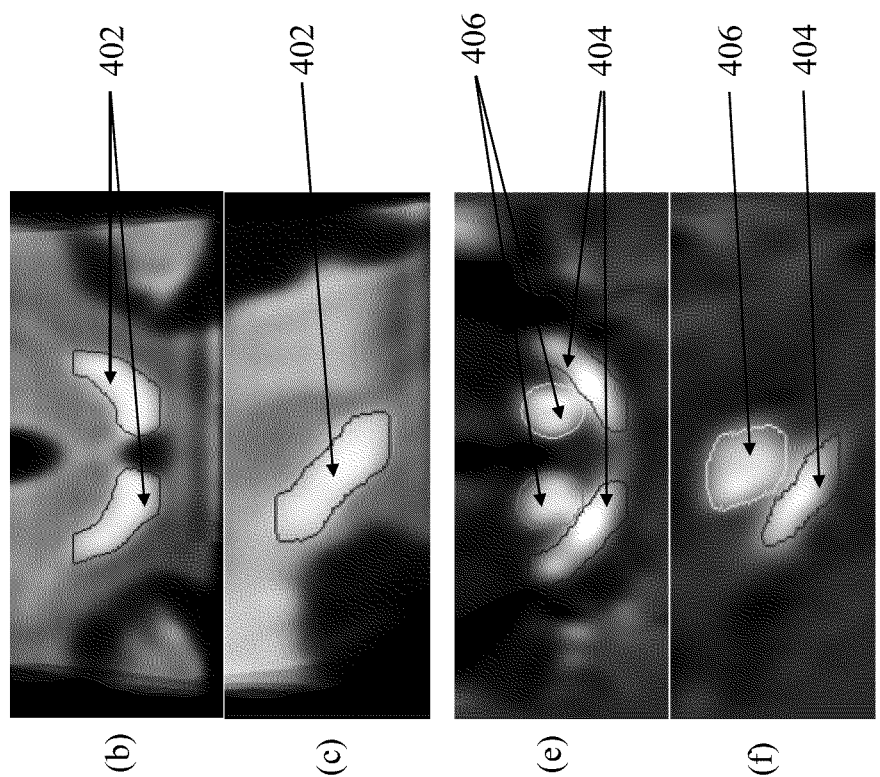
FIG. 4 shows magnetic resonance (MR) images depicting a perspective of the NM in the NM-MRI template space, and perspectives of SN, RN and STN in the QSM template space.
Figure 4:
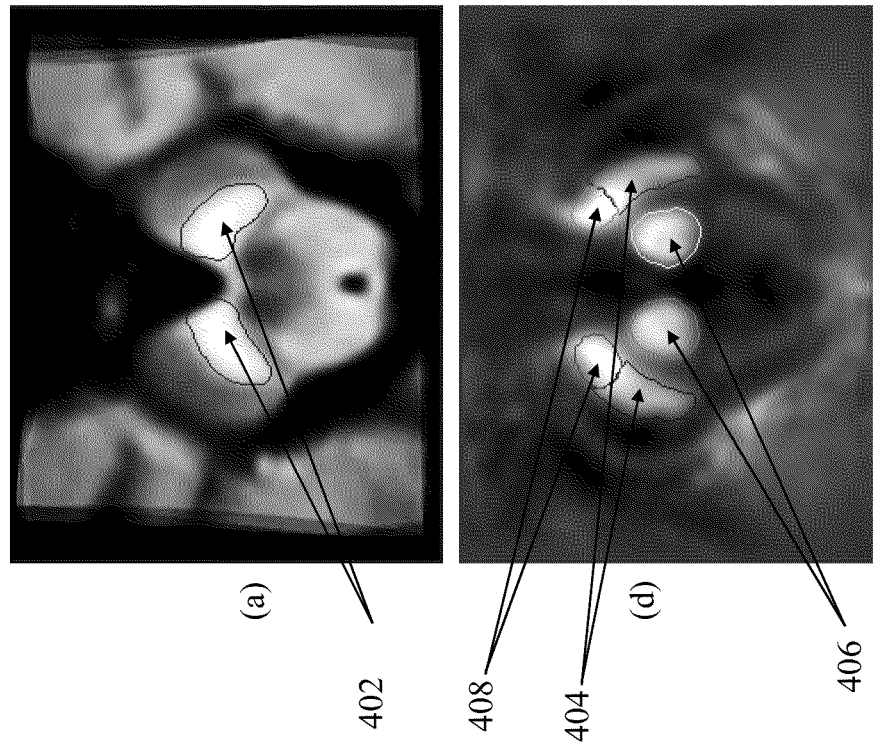

Referring to FIG. 4, MR images depicting a perspective of the NM in the NM-MRI template space and perspectives of SN, RN and STN in the QSM template space are shown. Specifically, images (a)-(c) illustrate various perspectives of the NM 402 in the NM-MRI template using the validation dataset. The boundaries of the NM 402 are drawn manually. The images (d)-(f) illustrate perspectives of the SN 404, RN 406 and STN 408. The boundaries of the SN 404, RN 406 and STN 408 in images (d)-(f) of FIG. 4 were drawn manually.

Figure 5:
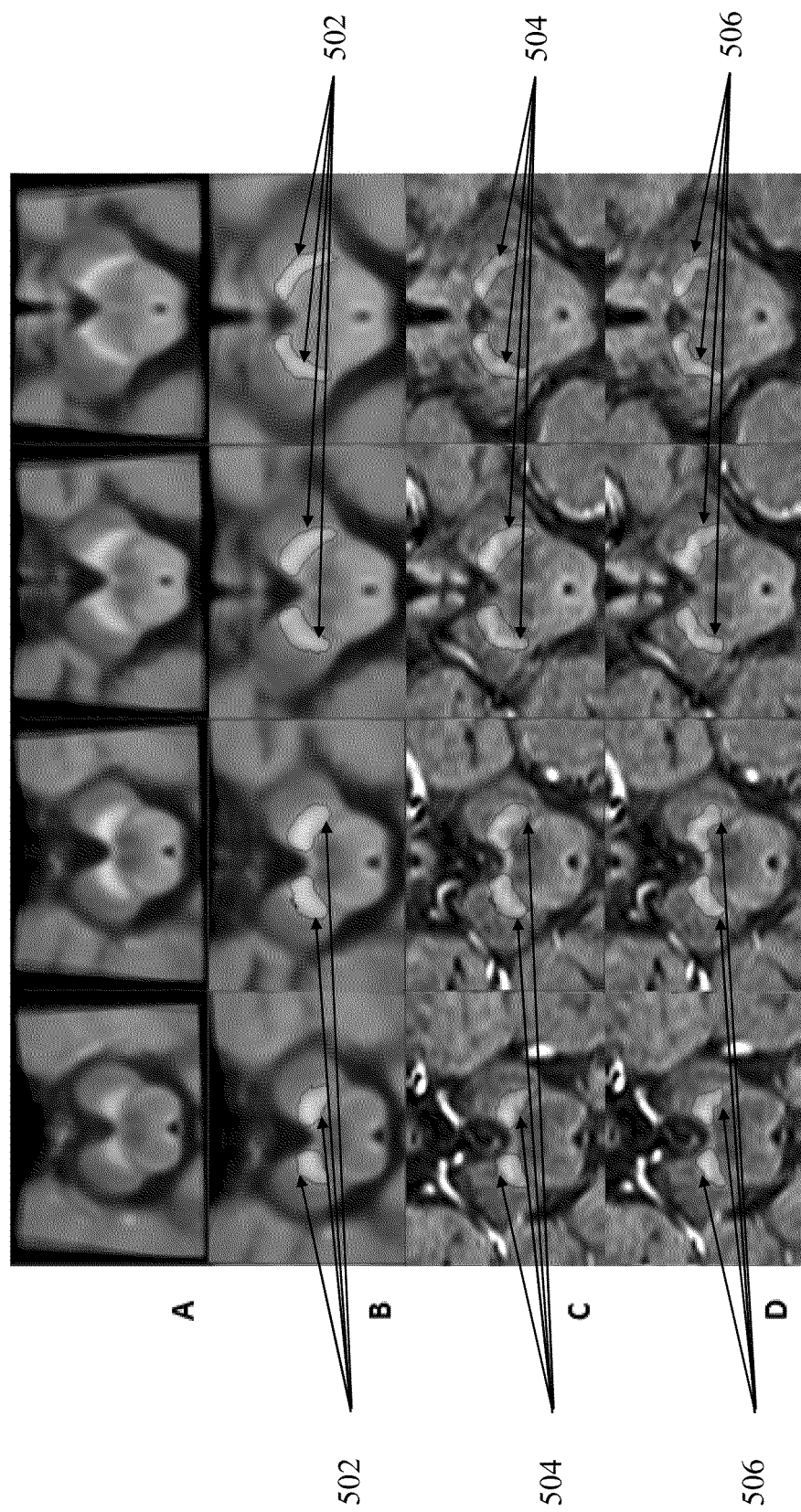
FIG. 5 shows images illustrating various steps for mapping NM boundaries to the original space from the template space.

Referring to FIG. 5, images illustrating various steps for mapping NM boundaries to the original space from the template space are shown. Specifically, the boundaries from 16 slices taken from every $12^{th}$ slice in the 0.167 mm isotropic template space are overlaid onto the original 2 mm thick midbrain slices are shown for the NM data. The boundaries only appear on 4 of these slices since the midbrain is only seen on these 4 slices. Each column of images in FIG. 5 represents a separate slice. The upper most row of images, denoted as row A, shows images of various slices of the constructed neuromelanin template. The second row (from the top), denoted as row B, shows the same images as in row A but with the neuromelanin DPA boundaries 502. The third row, denoted as row C, shows superimposed template boundaries 504 representing boundaries 502 transformed onto the original images 504. The final row, denoted as row D, shows the midbrain images of the subject with final boundaries 506 of the NM obtained by fine tuning the superimposed template boundaries 504 using the DPA.

Figure 6:
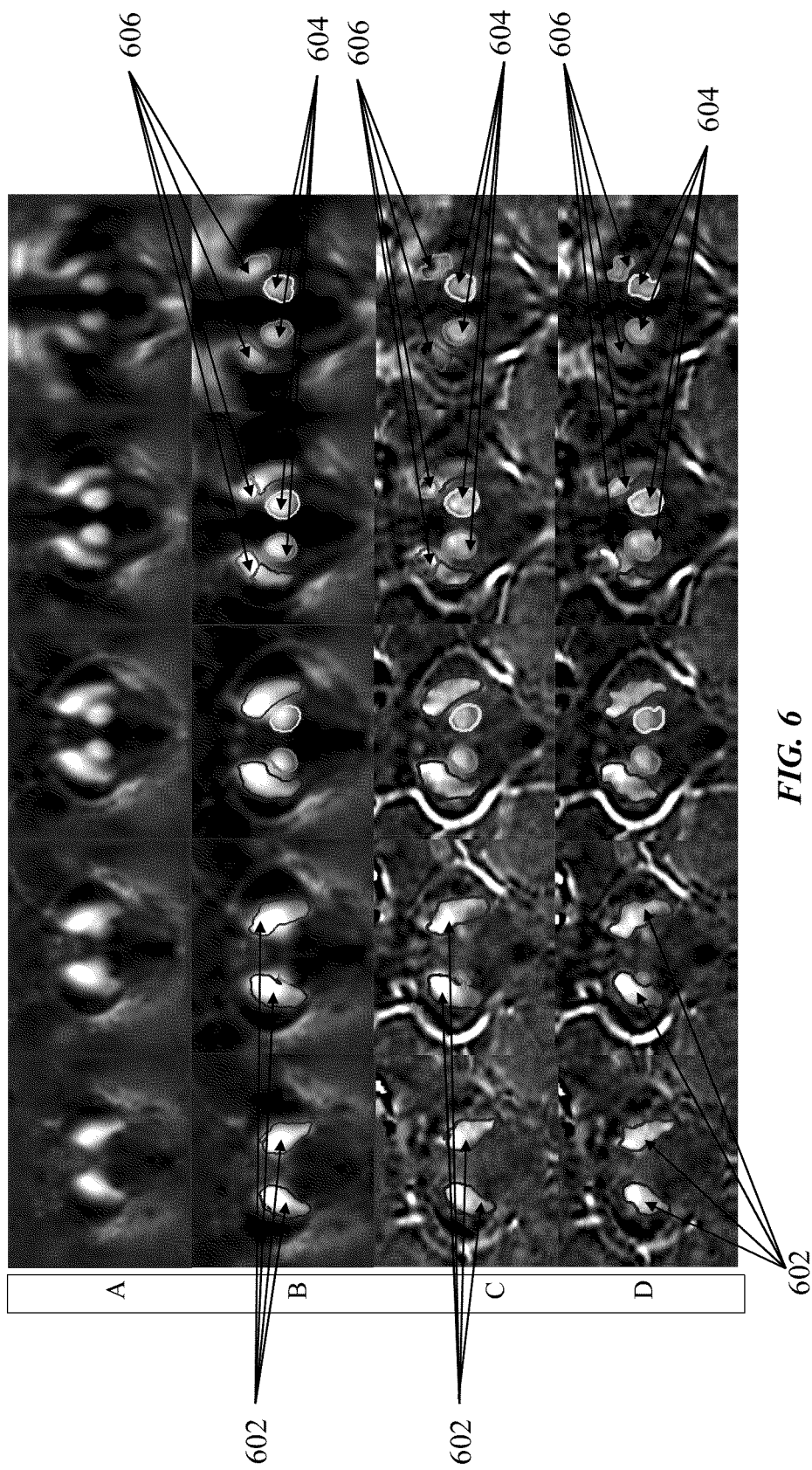
FIG. 6 shows images illustrating various steps for mapping SN, RN boundaries and STN boundaries from the template space to the original space.

Referring to FIG. 6, shows images illustrating various steps for mapping SN, RN and STN boundaries from the template space to the original image space for QSM data are shown. Each column represents a different slice. The first (upper most) row, denoted as row A, shows images depicting various slices of the constructed QSM template. The second row, denoted as row B, shows the same images with the QSM DPA boundaries for the SN 602, RN 604 and STN 606. The third row, denoted as row C, shows the boundaries transformed to the original space for the SN 602, RN 604 and STN 606. The final row, denoted as row D, shows the images depicting various midbrain slices of the subject with the final boundaries of the SN 602, RN 604 and STN 606 obtained after applying DPA to the boundaries in row C.

With regard to the initial training of the template, 30 cases were processed for the MTC and QSM data. The integrity of the template automatic MTC background intensity is demonstrated by the fact that the slope relating one to the other is 0.99, with an $R^2$ of 0.53, and a p-value<0.001. The background values are key to properly thresholding the NM and iron content signals.

Figure 7A:
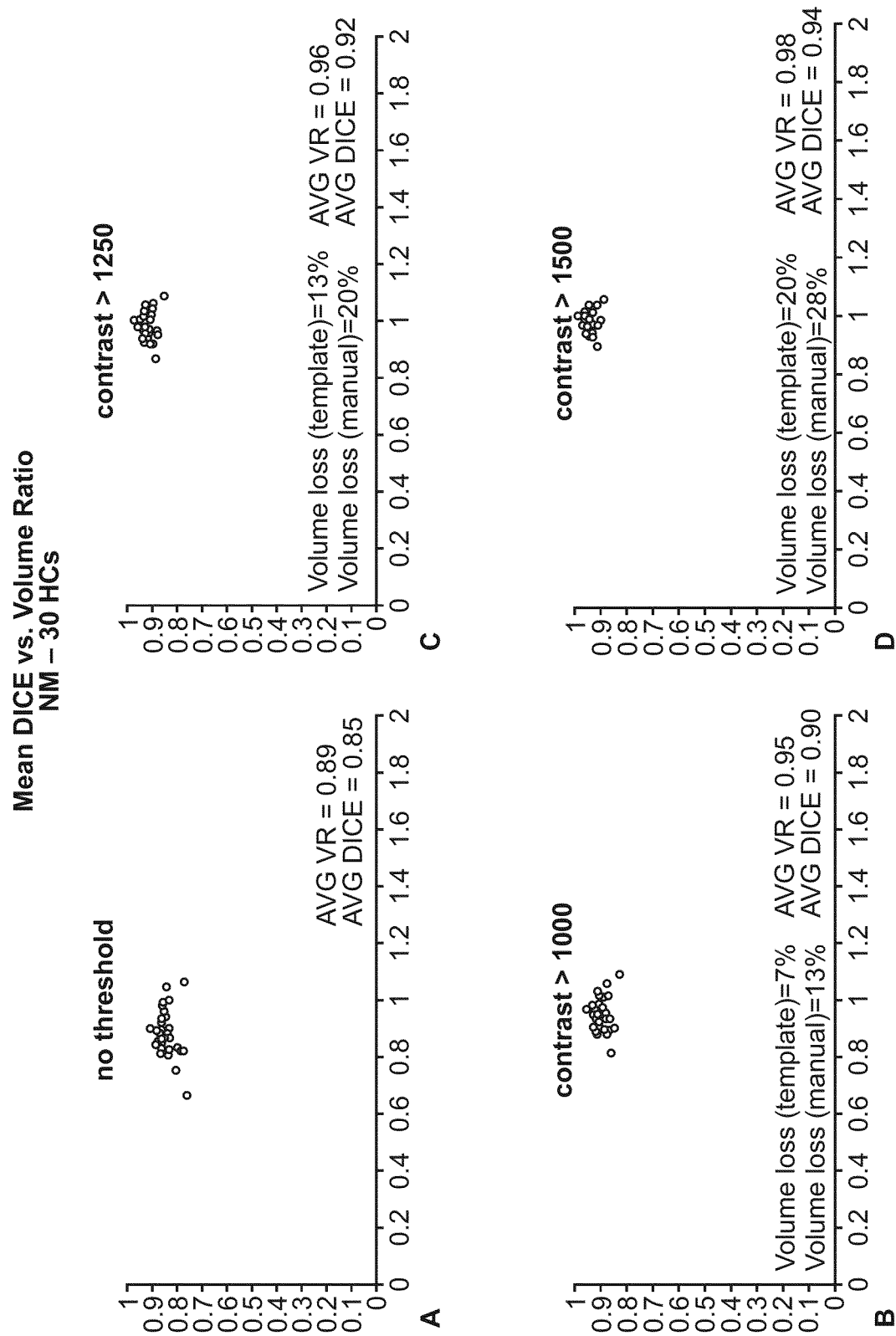
FIGS. 7A and 7B show DICE similarity coefficients plotted against volume ratio values for the neuromelanin (NM) based on various scenarios.
Figure 7B:
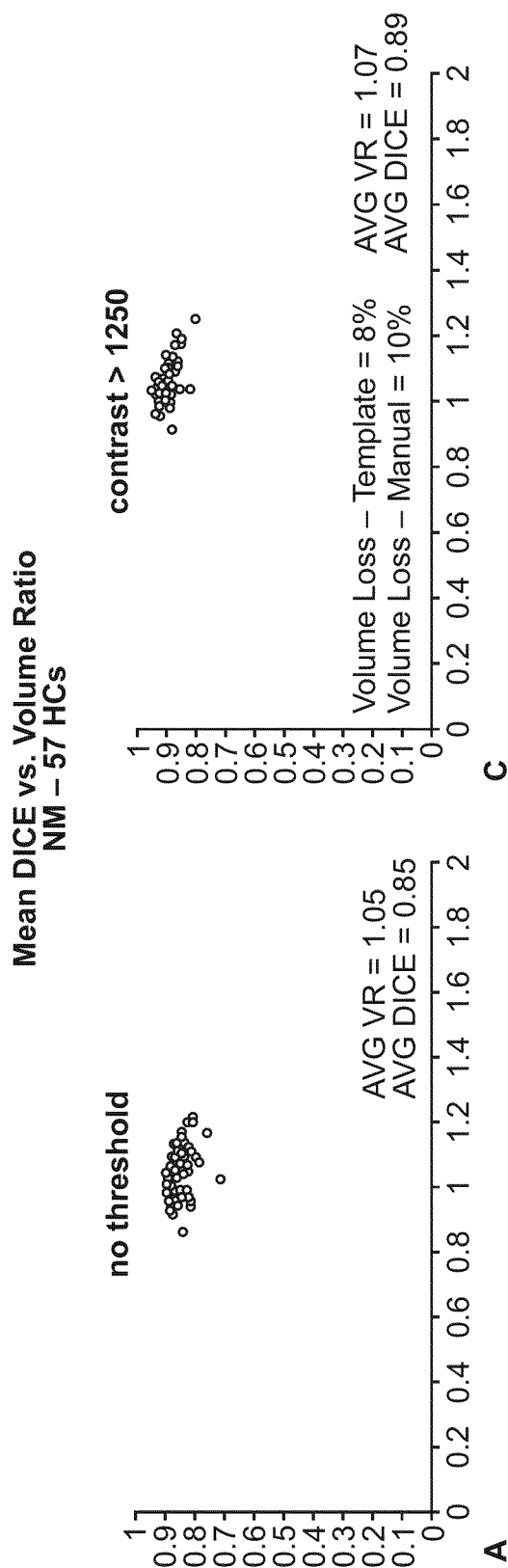
Figure 7B:
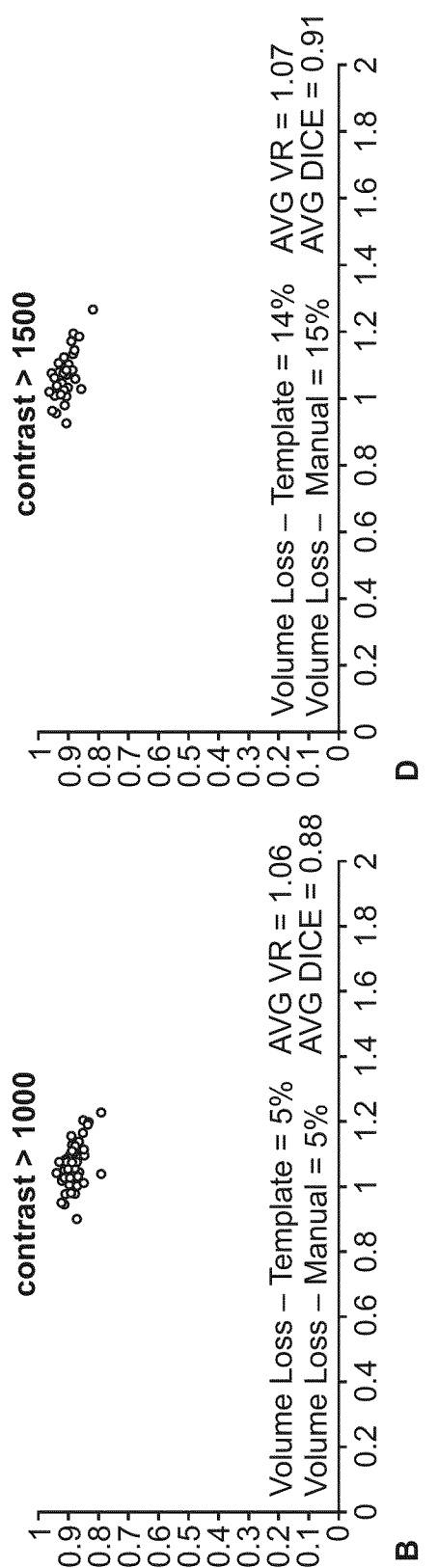

The DICE similarity coefficients and volume ratio (VR) measures were made for different thresholds for both MTC and QSM images, and the data associated with the NM and SN DICE coefficients plotted against the VR are shown in FIGS. 7A-7B and 8A-8B, respectively. Referring to FIGS. 7A and 7B, plots of DICE similarity coefficients plotted against VR values for the neuromelanin (NM) are shown based on various scenarios. In both FIGS. 7A and 7B, plot A corresponds to the scenario of no threshold applied, plot B corresponds to a threshold for NM contrast larger than 1000, plot C corresponds to a threshold for NM contrast larger than 1250, and plot D corresponds to a threshold for NM contrast larger than 1500. The plots in FIG. 7A are generated using the data for the 30 training cases, while the plots of FIG. 7B are generated using data for the 57 validation cases. The average DICE, volume ratio, and volume loss associated with the template and manually drawn data are quoted for each threshold. A threshold of 1000 units keeps the volume loss minimal and yields excellent results.

Figure 8A:
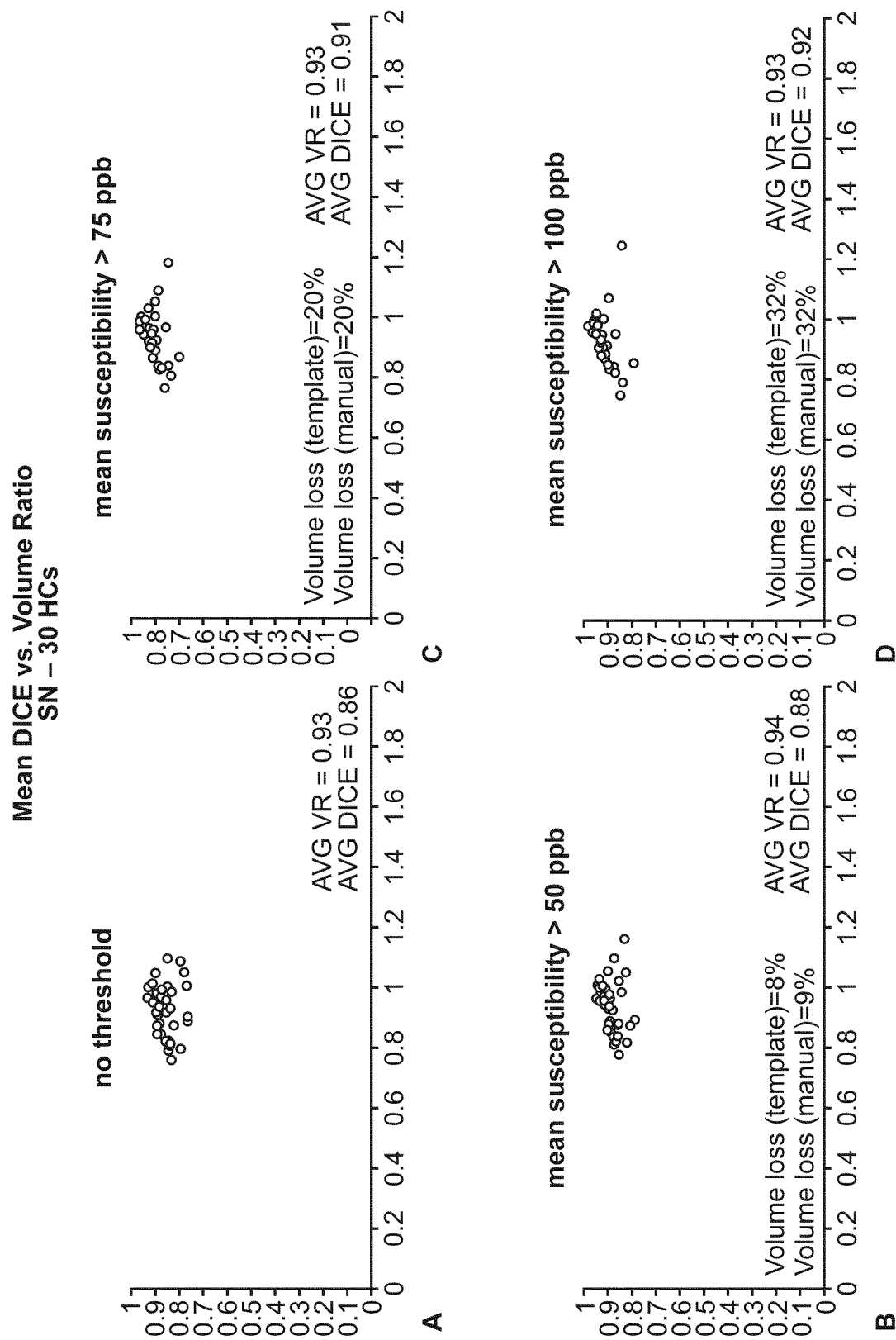
FIGS. 8A and 8B show DICE similarity coefficients plotted against volume ratio values for the substantia nigra (SN) based on various scenarios.
Figure 8B:
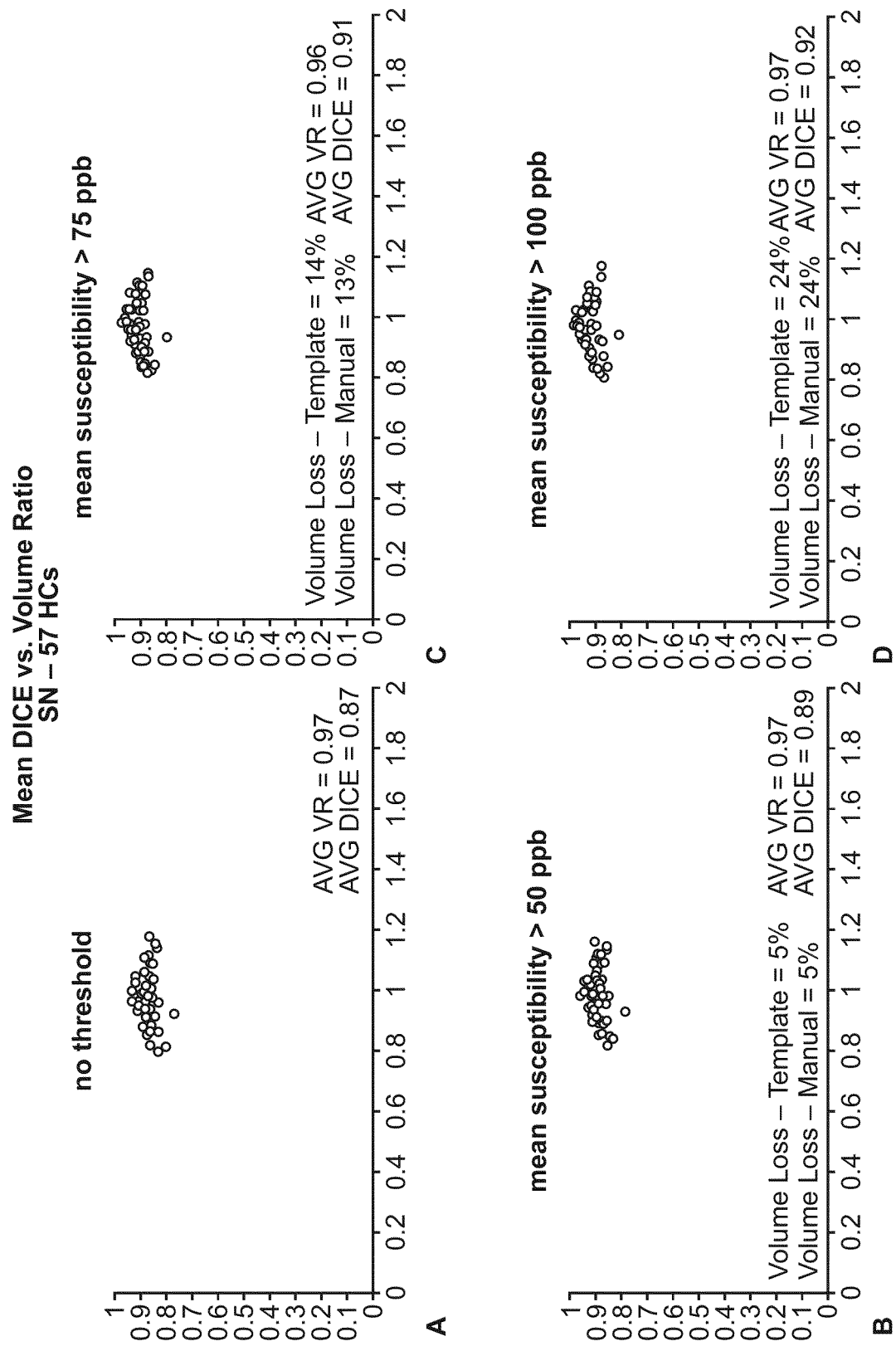

Referring to FIGS. 8A and 8B, plots of DICE similarity coefficients plotted against VR values for the SN are shown based on various scenarios. In both FIGS. 8A and 8B, plot A corresponds to the scenario of no threshold applied, plot B corresponds to a threshold for susceptibility values larger than 50 ppb, plot C corresponds to a threshold for susceptibility values larger than 75 ppb, and plot D corresponds to a threshold for susceptibility values larger than 100 ppb. The plots in FIG. 8A are generated using the data for the 30 training cases, while the plots of FIG. 8B are generated using data for the 57 validation cases. The average DICE, volume ratio, and volume loss associated with the template and manually drawn data are quoted for each threshold. A threshold of 50 ppb yields minimal loss in the SN volume.

The higher the threshold, the tighter the distribution becomes in theory eventually approaching unity on both axes. However, the higher thresholds also cause higher loss in volume. Therefore, there has to be a tradeoff between satisfactory DICE and volume ratios with volume loss. For the NM contrast, with a threshold of 1000, the average volume loss of template data for all the cases is less than 10% yielding average DICE and VR values of 0.90 and 0.95, respectively. Higher thresholds such as 1250, yielded an average volume loss slightly over 10% (average DICE=0.92; average VR=0.96), and the data showing NM contrast of over 1500 yielded an average loss of 20% with relatively higher DICE and VR than the lower thresholds (0.94 and 0.98, respectively). The threshold of 1000 is seen to keep the volume loss below 10% while resulting in acceptable DICE and VR values. Similarly, as shown in FIGS. 8A-8B for the SN, a mean susceptibility threshold of 50 ppb yielded an average volume loss just under 10% while the average DICE and VR values were 0.88 and 0.94, respectively.

Figure 9:
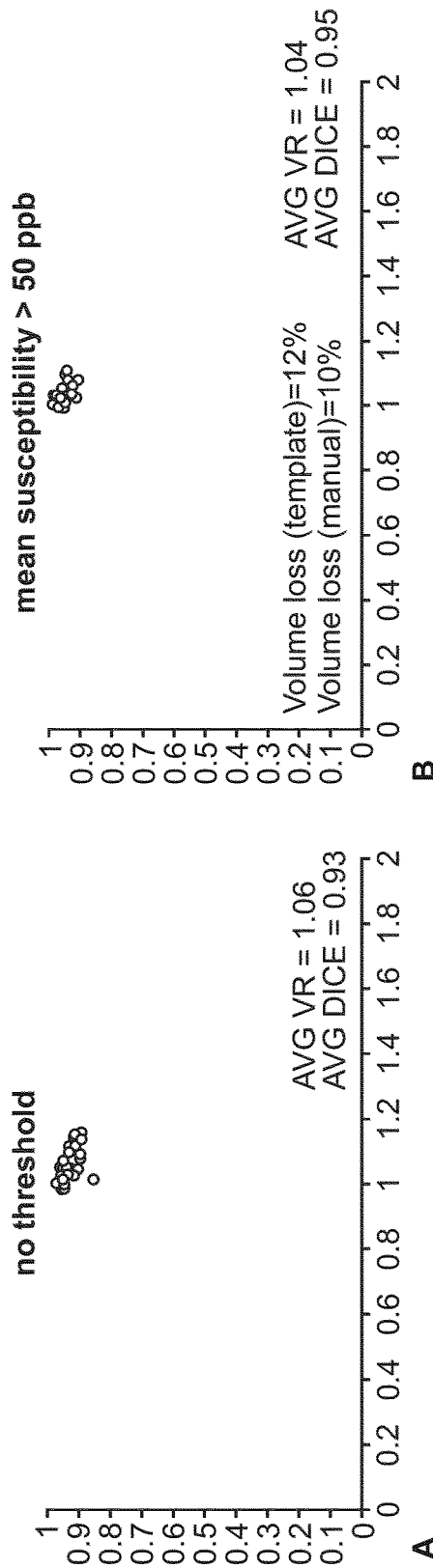
FIG. 9 shows DICE similarity coefficients plotted against volume ratio values for the red nucleus (RN) based on various scenarios.
Figure 9:
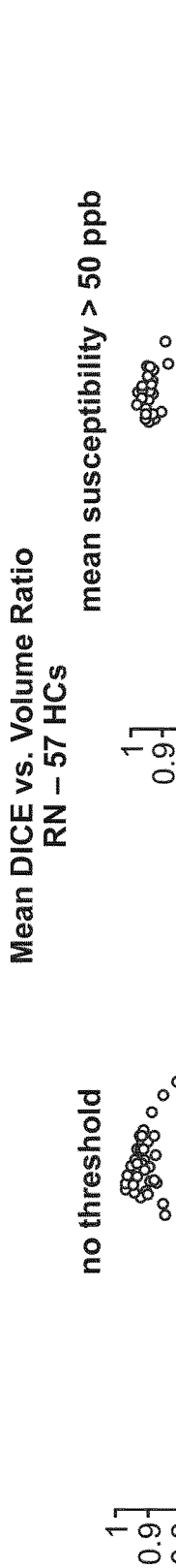

FIG. 9 shows plots of DICE similarity coefficients plotted against VR values for the red nucleus (RN) based on various scenarios. Plots A (left column) correspond to the scenario where no threshold is applied, while plots B (right column) corresponds to the scenario where a threshold of 50 ppb is applied. The plots in the top row are generated using the dataset of the 30 training cases, while the plots in the bottom row are generated using the dataset of the 57 validation cases. The average DICE, volume ratio, and the volume loss associated with the template and manually drawn data for the selected threshold are quoted within each plot. The threshold of 50 ppb limits volume loss to roughly 10%.

Figure 10:
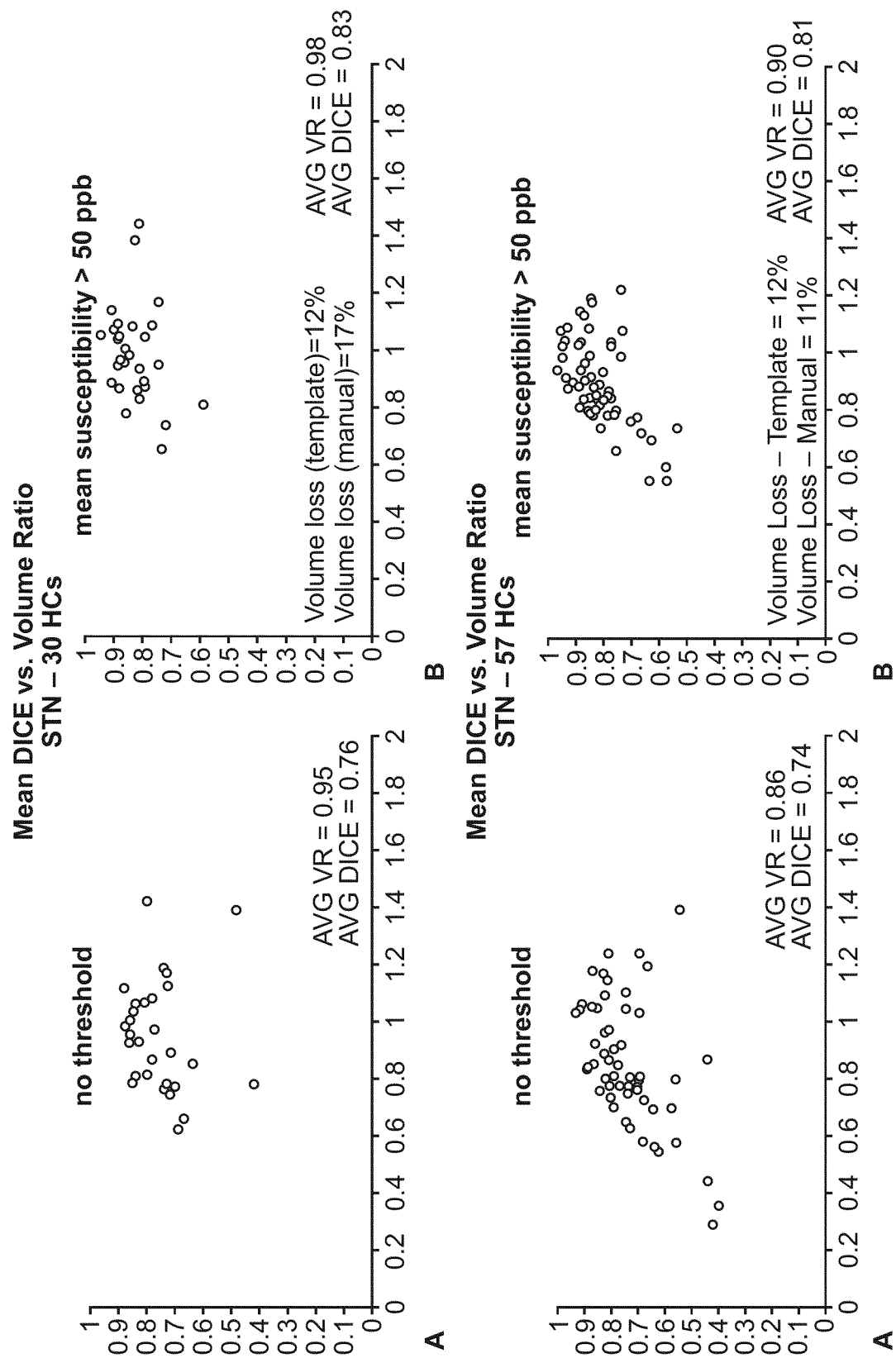
FIG. 10 shows DICE similarity coefficients plotted against volume ratio values for the subthalamic nucleus (STN) based on various scenarios.

FIG. 10 shows plots of DICE similarity coefficients plotted against VR values for the subthalamic nucleus (STN) based on various scenarios. Plots A (in left column) represent a scenario where no threshold is applied, while plots B (right column) represent a scenario of a threshold of 50 ppb. The plots in the top row are generated using the dataset of the 30 training cases, while the plots in the bottom row are generated using the dataset of the 57 validation cases. The average DICE, volume ratio, and the volume loss associated with the template and manually drawn data for the selected threshold are quoted within each plot. The 50 ppb threshold keeps the volume loss to about 10%.

With regard to FIGS. 9 and 10, before applying any threshold on the QSM data, the average DICE and volume ratio were 0.93 and 1.06 for the RN, and 0.76 and 0.95 for the STN. However, applying a threshold of 50 ppb on the QSM data, yields an average DICE and VR of 0.95 and 1.04 for the RN, and 0.83 and 0.98 for the STN. An average VR larger than one indicates that most of the structures found by the fully automated template/DPA approach tended to be larger than those in the manual/DPA approach.

Figure 11:
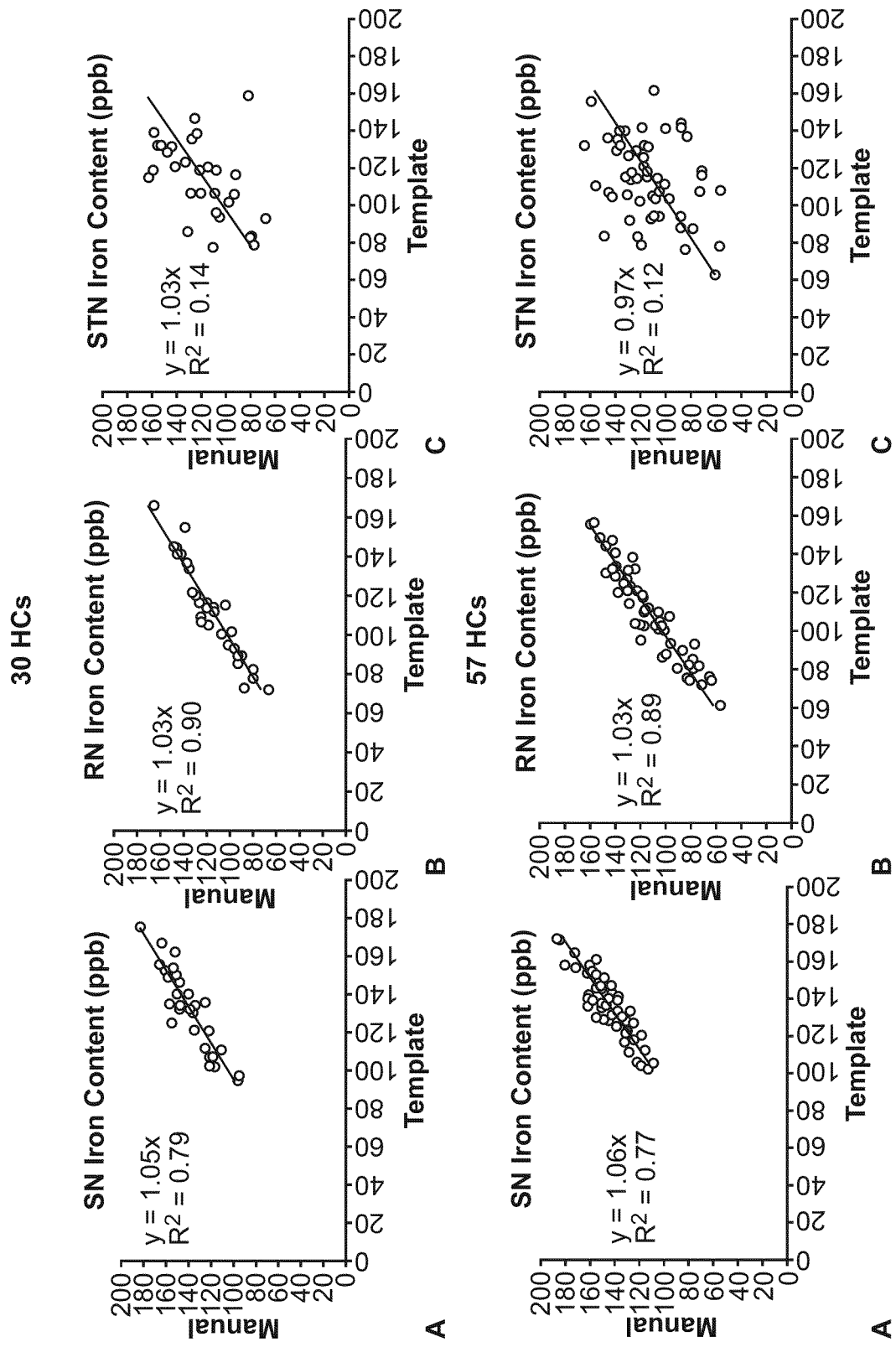
FIG. 11 shows plots illustrating the correlation between the SN, RN and STN iron content resulting from the manual and template segmentations for the 30 training cases (upper plots) and 57 validation cases (lower plots)

Referring to FIG. 11, plots illustrating the correlation between the SN, RN and STN iron content resulting from the manual and template segmentations are shown. Correlation between the SN, RN and STN iron content resulting from the manual and template segmentations for the 30 training cases is shown in the upper plots, while the correlation between the SN, RN and STN iron content resulting from the manual and template segmentations for the 57 validation cases is shown in the lower plots. Using the ROIs associated with the SN, RN and STN and a threshold of 50 ppb, the final outcome of the template versus manual drawings for the iron content is shown in the various plots. For each of the SN, RN and STN structures, the slope and $R^2$ are shown in each of the plots of FIG. 11. The p-values are less than 0.001 for the SN and RN and equal to 0.006 for the STN.

With regard to validation of the template, the validation dataset included 57 cases that were used in processing the QSM and MTC data. The DICE similarity coefficients were plotted against the VR values for both NM and SN and these results are shown in FIGS. 7B and 8B, respectively. For the NM contrast, with a threshold of 1000, the average volume loss of the template data for all the cases was about 5% yielding an average DICE and VR values of 0.88 and 1.06, respectively. Similarly, for the mean susceptibility of the SN, a threshold of 50 ppb yielded an average volume loss of almost 5% while the average DICE and VR values were 0.89 and 0.97, respectively. Similar to the previous dataset, thresholds of 1000 for the NM contrast and 50 ppb for the mean susceptibility of the SN yielded satisfactory results in terms of the average DICE, VR and volume loss over the 57 cases.

The DICE similarity coefficient versus VR for the RN and STN, are shown in FIGS. 9 and 10, respectively. Before applying any threshold on the QSM data, the average DICE and VR values were 0.92 and 1.05, and 0.74 and 0.86 for the RN and STN, respectively. Similar to the results from the previous dataset, applying a threshold improved these values. Using a threshold of 50 ppb on the QSM data yielded an average DICE and VR of 0.95 and 1.03, and 0.81 and 0.90 for the RN and STN, respectively, and a template average volume loss of around 12% for both structures.

FIG. 11 shows the correlation between the SN, RN and STN iron content for template and manual data. The corresponding slope and $R^2$ are shown in FIG. 10 for each structure. The p-values are <0.001 for the SN and RN and equal to 0.008 for the STN. Table 1 below summarizes the results associated with the estimated template volumes, VR measures and DICE similarity coefficients for each structure. The mean and standard deviation values are shown for the first and second datasets as well as for the merged data.

TABLE 1

Volume estimates, DICE similarity coefficients and volume ratio (VR) mean and standard deviation (SD) values per structure.

|  |  | Volume (mm³) | | VR | | DICE | |
| --- | --- | --- | --- | --- | --- | --- | --- |
|  |  | Mean | SD | Mean | SD | Mean | SD |
| NM | Dataset 1 | 299.36 | 26.11 | 0.89 | 0.08 | 0.85 | 0.03 |
|  | Dataset 2 | 291.05 | 27.51 | 1.05 | 0.08 | 0.85 | 0.03 |
|  | Overall | 293.92 | 27.17 | 0.99 | 0.11 | 0.85 | 0.03 |
| SN | Dataset 1 | 479.41 | 49.79 | 0.93 | 0.09 | 0.86 | 0.04 |
|  | Dataset 2 | 493.09 | 47.77 | 0.97 | 0.09 | 0.87 | 0.03 |
|  | Overall | 488.37 | 48.63 | 0.95 | 0.09 | 0.87 | 0.03 |
| RN | Dataset 1 | 191.9 | 25.90 | 1.06 | 0.05 | 0.93 | 0.03 |
|  | Dataset 2 | 193.72 | 32.28 | 1.05 | 0.07 | 0.92 | 0.03 |
|  | Overall | 193.09 | 30.09 | 1.05 | 0.07 | 0.92 | 0.03 |
| STN | Dataset 1 | 87.32 | 24.27 | 0.95 | 0.19 | 0.76 | 0.11 |
|  | Dataset 2 | 80.14 | 24.15 | 0.86 | 0.22 | 0.74 | 0.13 |
|  | Overall | 82.61 | 24.29 | 0.89 | 0.22 | 0.75 | 0.12 |

In the study described with regard to FIGS. 4-12, NM and QSM images derived from a single sequence (in less than 5 minutes) were used for the auto-segmentation of the SN, STN and RN in the original space, with no need to manually draw ROIs for the non-template based subjects. A multi-contrast atlas in combination with a DPA for boundary detection in both the template space and in the original images after transformation back from the template space are described and validated. Both DICE values and volume ratios showed excellent agreement for the volume and iron content measures between the automatic template approach versus the manual drawings.

Most existing templates do not include the NM, SN, STN and RN and do not a resolution as high as that presented in this work. For example, the MNI template is 1 mm isotropic, while the approach described herein used interpolated 0.67 mm in-plane isotropic data and further interpolated it to 0.167 mm isotropic resolution in 3D. Practically, we found that using the whole brain global deformable registration with 0.67 mm isotropic resolution, using either ANTs or SpinITK, could not get morphological transformations that could successfully match the shape of the midbrain structures consistently across subjects Therefore, a local registration (also referred to herein as local transformation) step was added to solve this problem and lead to much improved results. From this local transformation approach, both iron and neuromelanin templates were created from a single multi-echo sequence.

Previous research has attempted to segment the SN by using structural MRI atlases based on T1 and/or T2 weighted sequences. However, the SN is a small structure in the midbrain with a low contrast in these images making it difficult to accurately define the SN boundaries. To overcome this limitation, some other studies tried to get the SN atlas using either the NM-MRI or QSM. By using a dynamic atlas composed of NM-enhanced brain images for the automatic segmentation of the SN, one group showed a DICE value of less than 0.75. The NM-sensitive T1-weighted fast spin-echo sequence applied in their study is not optimal to clearly delineate the SN. The contrast of the NM can be much improved by using an MT-MRI acquisition sequence. To the inventors' knowledge, no study has tried to use both NM-MRI and QSM to auto-segment the SN, SNpr and SNpc.

Previous studies have segmented the SN by including either younger (>5 and <18 years) or older (>60 years) subjects. The use of an atlas based on only younger healthy subjects may not be appropriate for studying patients with neurodegenerative diseases that affect the structure of the midbrain. These between-subject and within-subject age- and disease-related morphometric changes may be important and affect the success of using a template approach when localizing the SN. The most appropriate atlas for a given study is the one which requires the least amount of global or regional warping from native subject space to atlas space; therefore, we used elderly HC subjects (mean age. 63.4 years old) to create the atlas to study patients with neurodegenerative diseases. To alleviate the bias caused by inter-subject variability, some studies used a probabilistic atlas, and attempted to construct a probabilistic atlas of SNpc based on the NMS-MRI sequence to investigate the micro-structural abnormalities in the SNpc using diffusion MRI in PD patients. They applied a symmetric diffeomorphic registration for registering T1 images and the SNpc masks of 27HCs onto the MNI space and the atlas was thresholded at 50% probability. However, the average dice coefficient for the atlas versus human raters was less than 0.61 The thresholding values can lead to dramatic changes in the delineation of the NM, thus decreasing the reproducibility of the atlas.

In terms of the validation stage, the second data set shows that the DICE similarity coefficient and VR values are very close to those from the first dataset for structure; this confirms the consistency of the results generated by the automated template processing approach proposed herein. Also, the fact that these values are very close to unity shows the excellent performance of this approach.

In the approach described herein, a DPA (implementing an edge detection algorithm) is employed after creating a probabilistic atlas of the SNpc to further improve the validity of the NM atlas.

In conclusion, the new approach described herein for fully automatic segmentation of the deep gray matter in the midbrain (or anatomical structures in general) uses a template approach as a guide but uses the original data with a dynamic programming algorithm to fine tune the boundaries. With this approach, it is possible to quantify the neuromelanin in the SN and the volume and iron content for all of the SN, STN and RN This approach should make it possible to study the changes in these imaging biomarkers for a variety of neurodegenerative diseases without the need for manual tracing of these structures.

Figure 12:
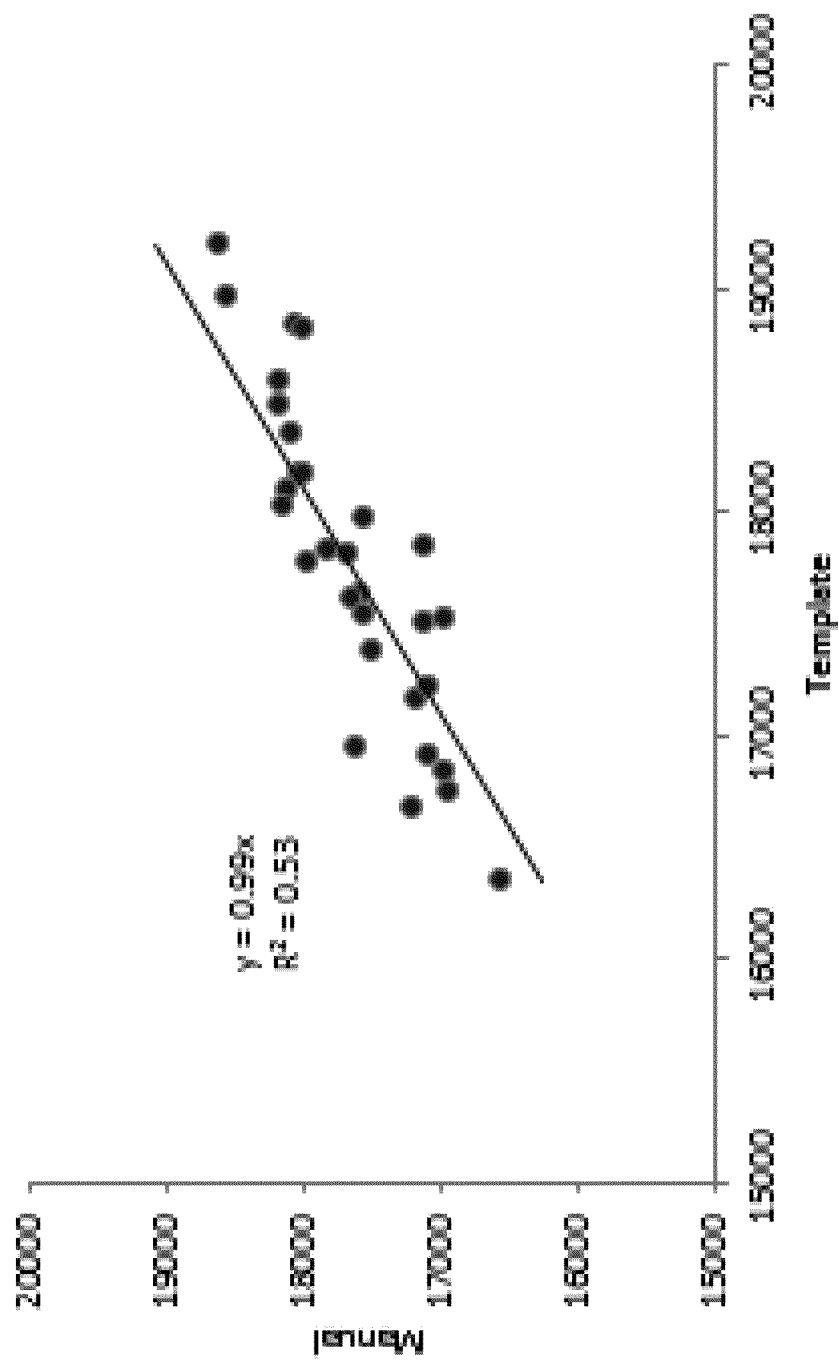
FIG. 12 shows plots depicting agreement between the manual and template neuromelanin (NM) background measurements for the 30 healthy controls.

With regard to neuromelanin (NM) background measurements and since the background values are key to properly thresholding the NM signals, 30 MTC cases were processed to obtain the neuromelanin (NM) background measurements Referring to FIG. 12, a plot depicting agreement between the manual and template neuromelanin (NM) background measurements for the 30 healthy controls (or training subjects) are shown. Specifically, the plot illustrates the integrity of the template automatic MTC background intensity measures relative to the manual drawings. The agreement between the manual and template MTC background measures shows a slope of 0.99, an $R^2$ of 0.53, and a p-value<0.001.

Figure 13:
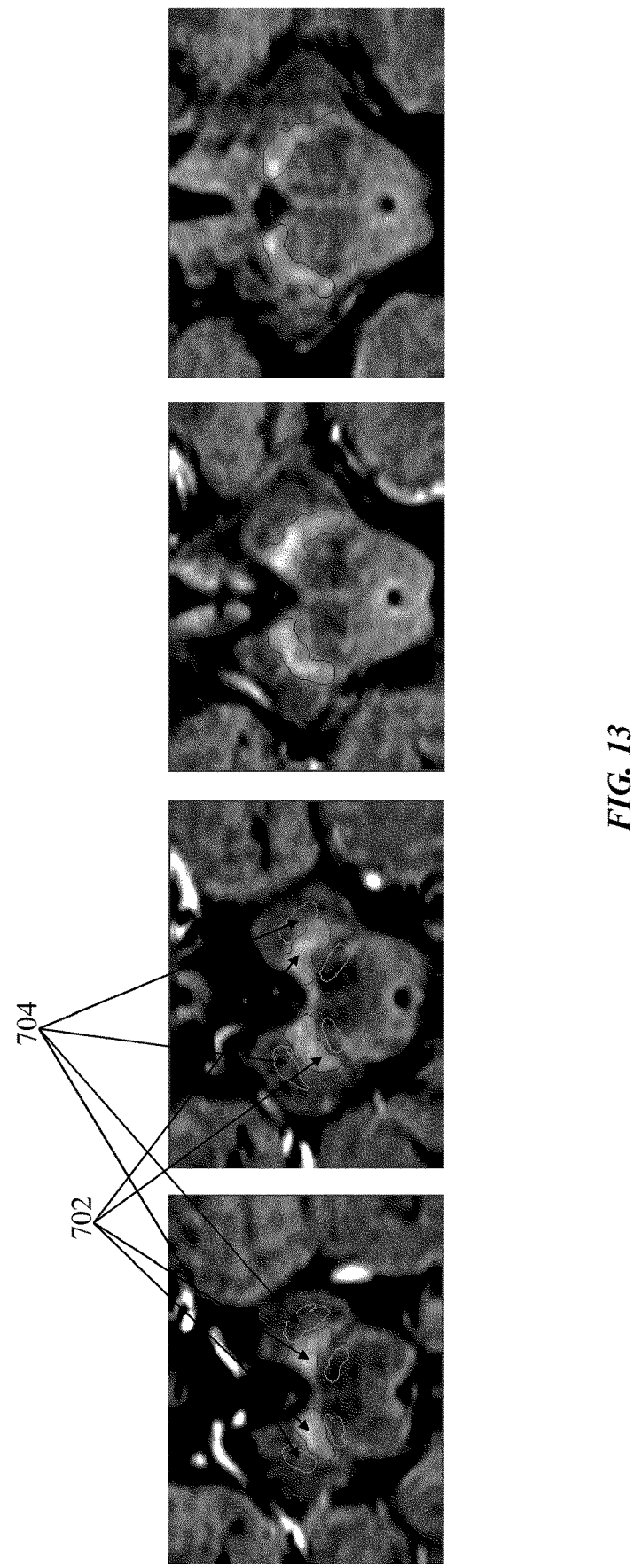
FIG. 13 shows images illustrating background boundaries relative to the NM boundaries identified using a dynamic programming algorithm (DPA)
Figure 14:
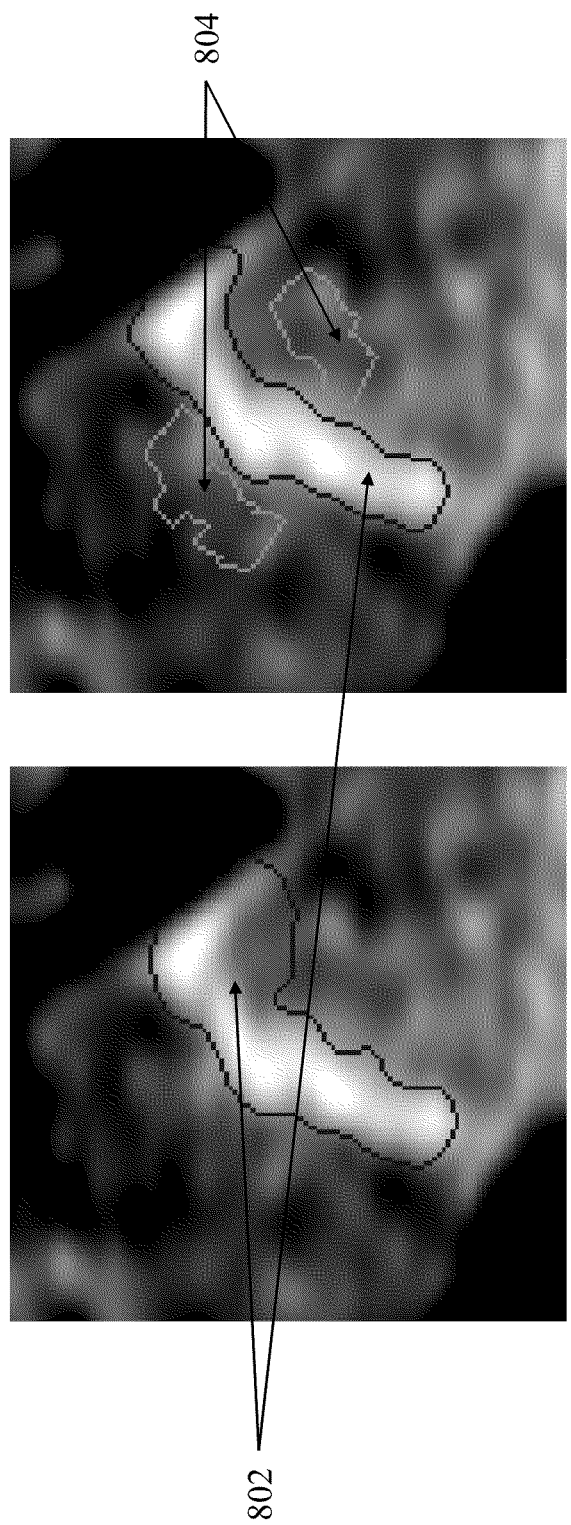
FIG. 14 shows images illustrating background boundaries after transformation from the template space to the original space and the NM DPA boundaries.

With regard to the DPA, the final template boundaries of all the structures of interest can be determined using the dynamic programming algorithm (DPA) for boundary detection in both the template space and the original space. Example detailed steps of the DPA algorithm can be as follows:
1. The initial boundary can be drawn on the template data for both NM and QSM.
2. The background can then be drawn on the template images as shown in FIG. 13. In FIG. 13, both the NM 702 and background regions 704 are shown.
3. The boundaries and background can then be transformed to the original space as shown in FIG. 14. In FIG. 14, the NM region 802 and the background region 804 are shown after transformation from the template space to the original space. Using the background value plus 1000 makes it easier to refine the DPA boundary to provide a faster convergence and to use a smaller and safer search radius to prevent the algorithm from leaking outside the original boundary
4. The background mean±4σ, where σ is the standard deviation of the background region of interest which in this study was found to be roughly 250 units, can be used as the threshold on the MTC data to remove all points lower than this threshold to determine the NM refined boundary. For the QSM data, the pixels with a susceptibility less than zero ppb can be removed before the DPA is run for all of the SN, STN and RN
5. A 3×3 Gaussian filter can be used to smooth the initial boundary.
6. The centerline can then be determined using a thinning method.
7. Boundary refinement prior to DPA: Since there can be some variation of intensity around the structure, the global threshold might not be good for the whole structure in the MTC data. Therefore, Otsu's method [reference: 1979 IEEE "A Threshold Selection Method from Gray-Level Histograms", Nobuyuki Otsu] can be on the filtered local image in a 40×40 pixel square around each single centerline point and all points lower than the Otsu threshold can be removed. If the initial boundary is outside the boundary obtained by the Otsu threshold, the boundary can be modified to those nearest points that remain (referred to as the Otsu boundary) This step helps DPA converge faster.
8. Implementing DPA: For each point along the centerline, the DPA can be run in the corresponding search box. To allow for curved shapes, the center of the centerline can be used to determine the initial rays. Then DPA can be applied for the next set of rays by shifting one pixel along the centerline associated with the initial boundary. For each DPA iteration, the centerline can be updated. Once the endpoint is reached, these rays can be swept through 180°. Then the algorithm can return along the centerline until it reaches the opposite endpoint sweeping through another 180°. Finally, the center point can move back along the centerline returning to the starting point to close the boundary. This process can be repeated five times searching both inside and outside the boundary for the best result. For the NM, STN and the SN, this step can be followed by five more iterations using only an inside search.

The cost function used in this DPA includes a derivative term as well as a radius of curvature term which avoids the leakage of the structure of interest into the adjacent objects, although the search radius was limited to four pixels both inside and outside the boundary in the zoomed space. For points outside the boundary, when searching from the centerline outward, negative derivative values were set to zero. This restriction prevented the boundary from leaking out into nearby bright objects. The cost function is given by:

$$C(r, m) = \frac{G(r, m) + G_{pre}}{G_{max}} - \alpha * \frac{|R(r, m) - R_{avg}|}{R_{avg}}$$

where $$G_{pre} = \sum_{t=m-3}^{m-1} G(t)_{max}$$

and the gradient and the radius along the $m^{th}$ ray at the $r^{th}$ point are denoted by G(r, m) and R(r, m), respectively. The term $G_{max}$ represents the maximum derivative inside the image and $R_{avg}$ is the average radius over the previous three radii. The constant α represents the relative weighting of the derivative and radius terms which can be set to values between 0 and 1. The closer the shape of the structure of interest is to a circle, the higher α can be set. If there are sharp edges, these can be smoothed by a large choice for α. Values of α between 0.05 and 0.15 all did a similar job in finding the edges faithfully, so a value of α=0.1 was chosen to be conservative.

Figure 15:
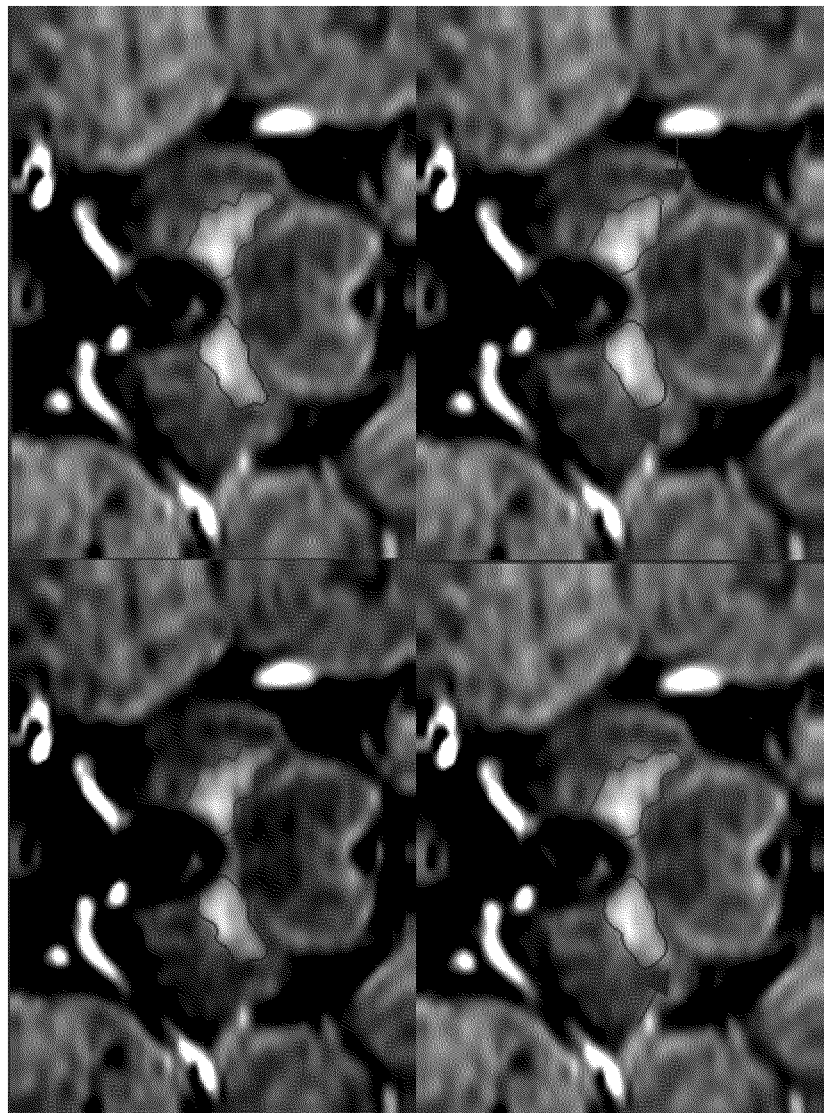
FIG. 15 shows images illustrating boundaries reconstructed with different values of the parameter α of the DPA.

Referring to FIG. 15, images illustrating boundaries reconstructed with different values of the parameter α of the DPA are shown. The choice of α can dramatically affect the final DPA boundary. The NM boundaries in the upper left image are obtained using α=0.05 In the upper right image, the NM boundaries are determined using α=0.10. In the lower left image, the NM boundaries are obtained using α=0.15. In the lower right image, the NM boundaries are obtained using α=0.20. Note that lower values of α lead to less smoothing from the radius constraint, while larger values of α lead to more smoothing. Higher values of α tend to round out the structure and shrink it more toward a circle. Low values lead to a very jagged edged boundary. Finally, the candidate points for the new boundary can be selected by maximizing the above-mentioned cost function for each ray.

Figure 16:
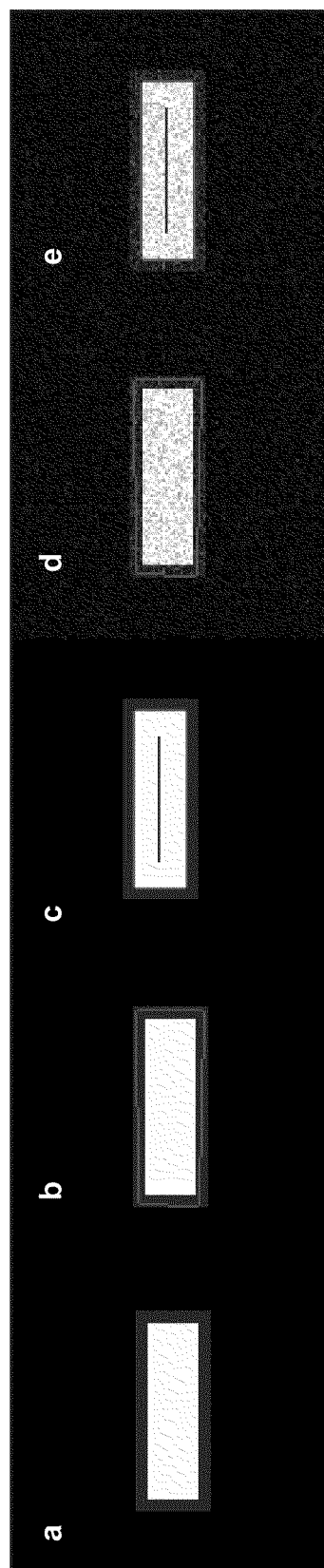
FIG. 16 shows simulation results for identifying the boundary of a rectangular region having two different intensities using the DPA.
Figure 17:
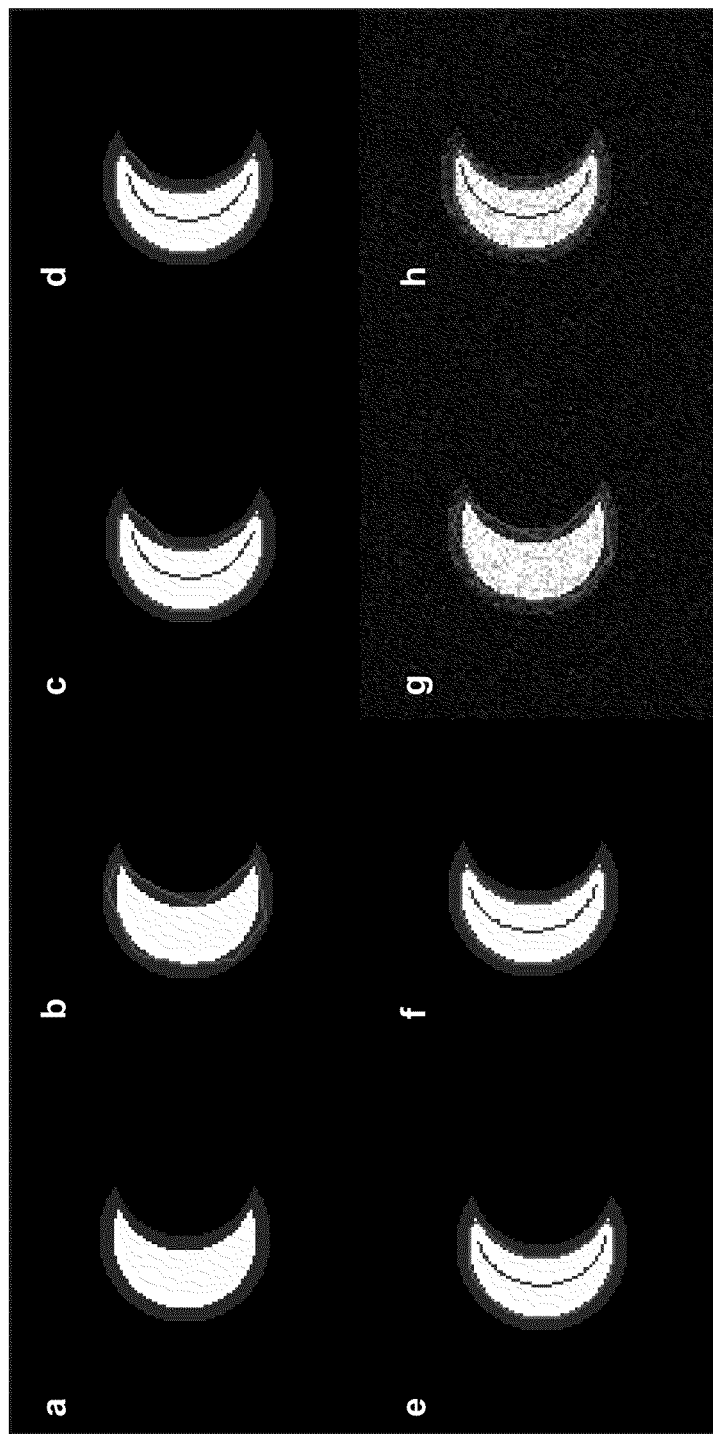
FIG. 17 shows simulation results for identifying the boundary of a crescent-shaped region having two different intensities using the DPA.
Figure 18:
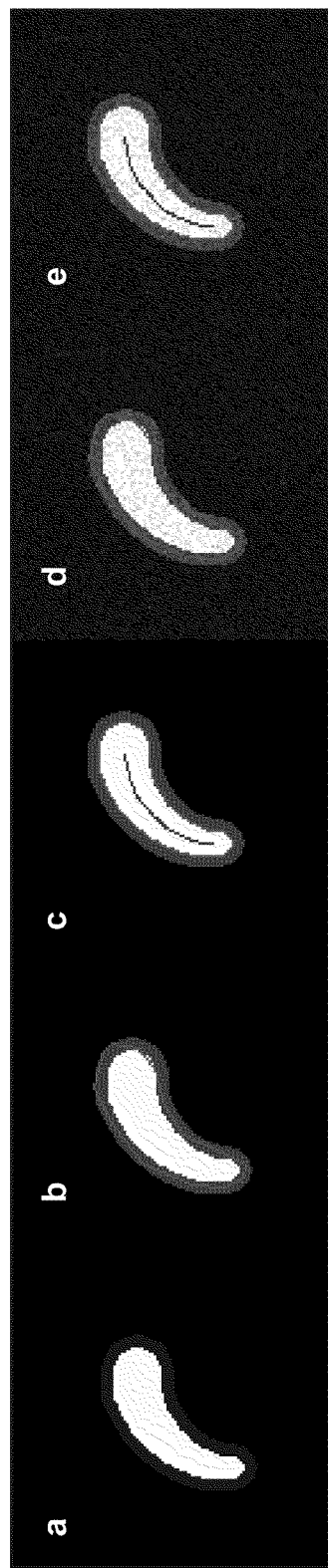
FIG. 18 shows simulation results for identifying the boundary of a cashew-shaped region having two different intensities using the DPA

Some example simulations are shown for different shapes in FIGS. 16-18. Referring to FIG. 16, simulation results for identifying the boundary of a rectangular region having two different intensities using the DPA are shown. Image (a) shows the rectangular region having two different intensities. Image (b) shows the rectangular region with a boundary drawn around the central area, and image (c) further shows the centerline found and the boundary updated after applying the DPA for 5 iterations. Image (d) is similar to image (b) except with noise added having a contrast-to-noise ratio (CNR) of 7:1 based on the difference in the signal intensities of the central region and the framed region within the second rectangular boundary. Image (e) shows the final boundary found after 5 iterations of the DPA which matches the correct area of 1400 pixels.

For the simulations corresponding to FIG. 16, the central region was set to 100 units, the outer framed area within the second boundary but outside the first boundary was set to 30 units and the background outside the second boundary was set to zero. Gaussian noise with a mean of zero and a standard deviation 10 units was added to the images. The first example of a rectangle with sharply defined corners and 1400 pixels is shown in FIG. 16. Despite the presence of noise, the boundary was still found perfectly.

FIG. 17 shows simulation results for identifying the boundary of a crescent-shaped region having two different intensities using the DPA. Image (a) shows the crescent-shaped region with two different intensities, and image (b) shows the same region was a boundary drawn around the central area of crescent-shaped region. Image (c) shows the crescent-shaped region with the corresponding centerline and the updated boundary after 5 iterations of DPA. Images (d) and (e) show updates of the centerline and the boundary after 10 iterations and 15 iterations of the DPA, respectively. Image (f) shows the centerline and the boundary after just 5 iterations when using the adaptive Otsu threshold approach. Image (g) is similar to image (c) with noise added where the CNR is 7:1, and image (h) shows the centerline and the boundary after just 5 iterations of the DPA when using the adaptive Otsu threshold approach.

The crescent-shaped region of FIG. 17 was chosen to mimic the more difficult case of detecting the boundary for a curved object. FIG. 17 shows the effects of running a different number of iterations. The mean after running a total of 35 iterations (image (f)) was found to be 990.5 with a standard deviation of 1.5 while using the Otsu approach in the presence of an SNR of 10:1 the mean was 984 and the standard deviation was 2.0.

FIG. 18 shows simulation results for identifying the boundary of a cashew-shaped region having two different intensities using the DPA. Image (a) shows the cashew-shaped region with two different intensities, and image (b) shows the cashew-shaped region with an initial boundary drawn around the central area. Image (c) shows the cashew-shaped region with the corresponding centerline and the boundary updated after 5 iterations of the DPA when using the adaptive Otsu threshold approach. Image (d) is similar to image (b) but with noise added where the CNR is 7:1. The final result of the boundary and the centerline after 5 iterations of the DPA when using the adaptive Otsu threshold approach and in the presence of noise is shown in image (e).

Finally, the cashew-shaped region of FIG. 18 was chosen to mimic the SN and evaluate the method when no sharp edges are present After running the initial 35 iterations, the mean was found to be 1086.5 and the standard deviation=2.5. Using the Otsu approach in the presence of a SNR of 10.1, and running another 30 iterations, the mean was found to be 1097 with a standard deviation of 0.0.

A person skilled in the art should appreciate that processes described in this disclosure can be implemented using computer code instructions executable by a processor. The computer code instructions can be stored on a non-transitory or tangible computer-readable medium such as a memory. The memory can be a random access memory (RAM), a read only memory (ROM), a cache memory, a disc memory, any other memory, or any other computer readable medium. Processes described in this disclosure can be implemented by an apparatus including at least one processor and/or memory storing executable code instructions. The code instructions when executed by the at least one processor can cause performing any of the processes or operations described in this disclosure. The apparatus can be, for example, an MRI scanner or a computing device.

What is claimed is:

1. A system comprising:
   one or more processors; and
   a memory, with computer code instructions stored thereon, the computer code instructions when executed by the one or more processors cause the one or more processors to:
   acquire a MR image of a subject with contrast illustrating one or more anatomical structures of interest;
   apply a global transformation to the MR image of the subject to generate a first morphed version of the MR image representing a first estimate of MR data of the subject in a template space;

apply a local transformation to the first morphed version of the MR image of the subject to generate a second morphed version of the MR image representing a second estimate of the MR data of the subject in the template space;

project boundaries of the one or more anatomical structures of interest from an anatomical template image onto the second morphed version of the MR image of the subject, the projected boundaries representing an estimate of the boundaries of the one or more anatomical structures of interest within the template space for the subject; and apply an inverse transformation to the estimate of the boundaries of the one or more anatomical structures of interest within the template space to determine a first estimate of corresponding boundaries of the one or more anatomical structures of interest in the MR image of the subject.

2. The system of claim 1, wherein the one or more processors are configured to:

use a boundary detection algorithm to fine tune the first estimate of the corresponding boundaries of the one or more anatomical structures of interest in the MR image of the subject and generate a second estimate of the corresponding boundaries of the one or more anatomical structures of interest in the MR image of the subject.

3. The system of claim 1, wherein the inverse transformation includes a concatenation of an inverse of the local transformation followed by an inverse of the global transformation.

4. The system of claim 1, wherein to apply the local transformation to the first morphed version of the MR image, the one or more processors are configured to apply the local transformation to a cropped region of the first morphed version of the MR image.

5. The system of claim 1, wherein to apply the local transformation to the first morphed version of the MR image, the one or more processors are configured to:

crop a region of the first morphed version of the MR image;

zoom the cropped region of the first morphed version of the MR image; and apply the local transformation to the zoomed cropped region of the first morphed version of the MR image.

6. The system of claim 1, wherein the MR image of the subject includes a quantitative susceptibility map (QSM) or a neuromelanin image.

7. The system of claim 1, wherein the one or more processors are configured to determine a volume of at least one of the one or more anatomical structures of interest, based on the corresponding boundaries of the one or more anatomical structures of interest in the MR image of the subject.

8. The system of claim 1, wherein the one or more processors are configured to determine a mean intensity of at least one of the one or more anatomical structures of interest, based on the corresponding boundaries of the one or more anatomical structures of interest in the MR image of the subject.

9. The system of claim 1, wherein the one or more processors are configured to determine a total signal of at least one of the one or more anatomical structures of interest, based on the corresponding boundaries of the one or more anatomical structures of interest in the MR image of the subject.

10. The system of claim 1, wherein the anatomical template image is generated using a plurality of MR images of a plurality of training subjects with contrast illustrating the one or more anatomical structures of interest.

11. A method comprising:

acquiring, by a computer system including one or more processors, a MR image of a subject with contrast illustrating one or more anatomical structures of interest;

applying, by the computer system, a global transformation to the MR image of the subject to generate a first morphed version of the MR image representing a first estimate of MR data of the subject in a template space;

applying, by the computer system, a local transformation to the first morphed version of the MR image of the subject to generate a second morphed version of the MR image representing a second estimate of the MR data of the subject in the template space;

projecting, by the computer system, boundaries of the one or more anatomical structures of interest from an anatomical template image onto the second morphed version of the MR image of the subject, the projected boundaries representing an estimate of the boundaries of the one or more anatomical structures of interest within the template space for the subject; and applying, by the computer system, an inverse transformation to the estimate of the boundaries of the one or more anatomical structures of interest within the template space to determine a first estimate of corresponding boundaries of the one or more anatomical structures of interest in the MR image of the subject.

12. The method of claim 11, comprising:

using a boundary detection algorithm to fine tune the first estimate of the corresponding boundaries of the one or more anatomical structures of interest in the MR image of the subject and generate a second estimate of the corresponding boundaries of the one or more anatomical structures of interest in the MR image of the subject.

13. The method of claim 11, wherein the inverse transformation includes a concatenation of an inverse of the local transformation followed by an inverse of the global transformation.

14. The method of claim 11, wherein applying the local transformation to the first morphed version of the MR image includes applying the local transformation to a cropped region of the first morphed version of the MR image.

15. The method of claim 11, wherein applying the local transformation to the first morphed version of the MR image includes:

cropping a region of the first morphed version of the MR image;

zooming the cropped region of the first morphed version of the MR image; and applying the local transformation to the zoomed cropped region of the first morphed version of the MR image.

16. The method of claim 11, wherein the MR image of the subject includes a quantitative susceptibility map (QSM) or a neuromelanin image.

17. The method of claim 11, comprising:

determining a volume of at least one of the one or more anatomical structures of interest based on the corresponding boundaries of the one or more anatomical structures of interest in the MR image of the subject.

18. The method of claim 11, comprising:

determining a mean intensity of at least one of the one or more anatomical structures of interest based on the corresponding boundaries of the one or more anatomical structures of interest in the MR image of the subject.

19. The method of claim 11, comprising:
determining a total signal of at least one of the one or more anatomical structures of interest based on the corresponding boundaries of the one or more anatomical structures of interest in the MR image of the subject.

20. A non-transitory computer-readable medium including computer code instructions stored thereon, the computer code instructions, when executed by one or more processors, cause the one or more processors to:
acquire a MR image of a subject with contrast illustrating one or more anatomical structures of interest;
apply a global transformation to the MR image of the subject to generate a first morphed version of the MR image representing a first estimate of MR data of the subject in a template space;
apply a local transformation to the first morphed version of the MR image of the subject to generate a second morphed version of the MR image representing a second estimate of the MR data of the subject in the template space;
project boundaries of the one or more anatomical structures of interest from an anatomical template image onto the second morphed version of the MR image of the subject, the projected boundaries representing an estimate of the boundaries of the one or more anatomical structures of interest within the template space for the subject; and
apply an inverse transformation to the estimate of the boundaries of the one or more anatomical structures of interest within the template space to determine a first estimate of corresponding boundaries of the one or more anatomical structures of interest in the MR image of the subject.

* * * * *